(12) United States Patent
Hillisch et al.

(10) Patent No.: US 7,550,451 B2
(45) Date of Patent: Jun. 23, 2009

(54) PROGESTERONE RECEPTOR MODULATORS WITH INCREASED ANTIGONADOTROPIC ACTIVITY FOR FEMALE BIRTH CONTROL AND HORMONE REPLACEMENT THERAPY

(75) Inventors: Alexander Hillisch, Jena (DE); Walter Elger, Berlin (DE); Gerd Schubert, Jena (DE); Birgitt Schneider, Jena (DE); Gudrun Reddersen, Jena (DE)

(73) Assignee: Bayer Schering Pharma AG, Berlin (DE)

( * ) Notice: Subject to any disclaimer, the term of this patent is extended or adjusted under 35 U.S.C. 154(b) by 62 days.

(21) Appl. No.: 10/631,967

(22) Filed: Aug. 1, 2003

(65) Prior Publication Data
US 2005/0026891 A1 Feb. 3, 2005

Related U.S. Application Data

(60) Provisional application No. 60/400,065, filed on Aug. 2, 2002.

(30) Foreign Application Priority Data
Aug. 2, 2002 (DE) .................. 102 36 405

(51) Int. Cl.
*A61K 31/56* (2006.01)
*C07J 1/00* (2006.01)
(52) U.S. Cl. .................. 514/179; 514/814; 552/642; 552/643; 552/648
(58) Field of Classification Search .......... 552/642, 552/643, 648; 514/179
See application file for complete search history.

(56) References Cited

U.S. PATENT DOCUMENTS

| 4,257,948 | A   |   | 3/1981  | Costerousse et al. |         |
|-----------|-----|---|---------|--------------------|---------|
| 4,536,401 | A   |   | 8/1985  | Neef et al.        |         |
| 5,089,635 | A   |   | 2/1992  | Neef et al.        |         |
| 5,693,628 | A   | * | 12/1997 | Schubert et al.    | 514/179 |
| 6,365,582 | B1  | * | 4/2002  | Schubert et al.    | 514/179 |
| 6,825,182 | B2  |   | 11/2004 | Ring et al.        |         |

FOREIGN PATENT DOCUMENTS

| DE | 35 04 421 A   |   | 8/1986  |
|----|---------------|---|---------|
| DE | 10221034 A1   |   | 5/2003  |
| EP | 0005100 B1    |   | 10/1979 |
| EP | 648 779 A     |   | 4/1995  |
| WO | WO 99/45023   | * | 9/1999  |
| WO | WO 01/15679 A |   | 3/2001  |
| WO | WO 01/26603 A |   | 4/2001  |
| WO | WO 01/34126 A |   | 5/2001  |

OTHER PUBLICATIONS

D. Loutradis et al., "Preovulatory effects of the progesterone antagonist mifepristone (RU486) in mice," Human Reproduction, 1991, vol. 6, No. 9, pp. 1238-1240.

K. Chwalisz et al., "Antiproliferative effects of progesterone antagonists and progesterone receptor modulators on the endometrium," Steroids, 2000, vol. 65, pp. 741-751.

O.D. Slayden et al., "Reversible suppression of menustration with progesterone antagonists in rhesus macaques," Human Reproduction, 2001, vol. 16, No. 8, pp. 1562-1574.

W. Elger et al., "Endocrine pharmacological characterization of progesterone antagonists and progesterone receptor modulators with respect to PR-agonistic and antagonistic activity," Steroids, 2000, vol. 65, pp. 713-723.

W. Elger et al., "Sulfamates of various estrogens are prodrugs with increased systemic and reduced hepatic estrogenicity at oral application," J. Steroid Biochem. Molec. Biol., 1995, vol. 55, No. 3/4, pp. 395-403.

E. M. Coutinho et al., "Is Menstruation Obsolete?" 1999, New York, Oxford University Press.

E.Isaksson et al., "Effects of oral contraceptives on breast epithelial proliferation," Breast Cancer Research and Treatment, 2001, vol. 65, pp. 163-169.

A. J. Spiegel et al., "Use of nonaqueous solvents in parenteral products," Journal of Pharmaceutical Sciences, Oct. 1963. vol. 52, No. 10, pp. 917-927.

Louis J. Ravin, "Preformulation," Bioavailability and Bioequivalency Testing, Chapter 75, pp. 1355-1497.

Dwight L. Deardorff, "Ophtalmic Preparations," Medicated Applications, Chapter 86, pp. 1498-1628.

G. Teutsch et al., 11Beta-substituted steroids, an original pathway to antihormones, 1988, vol. 31, No. 4B, pp. 549-565.

Xiang-Shu Fei et al., "New, convenient route four trifluoromethylation of steroidal molecules," J. Chem. Soc., Perkin Trans. 1, 1998, pp. 1139-1142.

Roussel-Uclaf, Bulletin Official de la Propriete Industrielle, No. 30. Pharmazeutische Technologie, 1961, Jahrgang 23 (Heft 2).

Arzneimittel, Synthetische s. Chemotherapie und Pharmakotherapeutica, *Ullmann's Encyclopedia of Technical Chemistry*, vol. 4, 1953.

International Search Report, PCT/EP03/08572, 2003.

* cited by examiner

*Primary Examiner*—Barbara P Badio
(74) *Attorney, Agent, or Firm*—Millen, White, Zelano, Branigan, P.C.

(57) ABSTRACT

The invention relates to new compounds of general formula I,

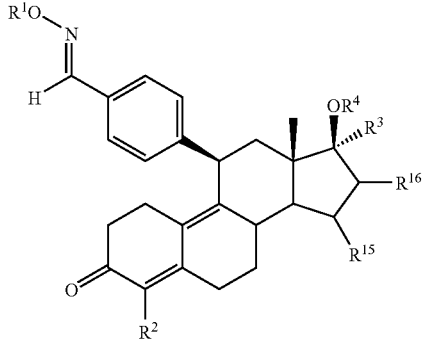

(I)

their production and pharmaceutical preparations that contain these compounds.

The compounds according to the invention are preferably used for female birth control and for HRT.

24 Claims, 11 Drawing Sheets

Tests on Antiluteolytic Activity After Subcutaneous Administration to Guinea Pigs

[Key:]
Uterusgewicht (mg) = Uterus weight (mg)
Vehikel = Vehicle
Onapriston = Onapristone
10mg/Tier/Tag = 10 mg/animal/day
Beispiel = Example Tests on Antiluteolytic Activity After Subcutaneous Administration to Guinea Pigs

[Key:]
Progesteron (ng/ml) = Progesterone (ng/ml)
Tag = Day
Vehikel = Vehicle
Onapriston = Onapristone
Beispiel = Example Tests on Androgenic Activity in Castrated Infant Male Rats After Subcutaneous Administration

[Key:]
Prostata (mg) = Prostate (mg)
Kontrolle = Control
Beispiel = Example

[Key:]
Samenblase (mg) = Seminal vesicle (mg)
Kontrolle = Control
Beispiel = Example Effects of Substances on FSH Levels in s.c. Administration

[Key:]
mg/Tier/Tag = mg/animal/day
Testosteronpropionat = Testosterone propionate
Beispiel = Example Effects of Substances on LH Levels in s.c. Administration

[Key:]
mg/Tier/Tag = mg/animal/day
Testosteronpropionat = Testosterone propionate
Beispiel = Example Tests on Osteoprotective Action After s.c. Administration (Alzet Pump) over 28 Days

[Key:]
Uterusgewicht (mg) = Uterus weight (mg)
µg/Tier/Tag = µg/animal/day
Beispiel = Example Tests on Osteoprotective Action After s.c. Administration

[Key:]
Knochendichte (mg/ccm) = Bone density (mg/ccm)
µg/Tier/Tag = µg/animal/day
Kontrolle = Control
Beispiel = Example Testing in the Gestagen Test in Infant Rabbits (McPhail Test)

[Key:]
mg/Tier/Tag = mg/animal/day
Vehikel = Vehicle
Progesteron = Progesterone
Beispiel = Example Testing in the Gestagen Test in Infant Rabbits (McPhail Test)

[Key:]
mg/Tier/Tag = mg/animal/day
Vehikel = Vehicle
Progesteron = Progesterone
Beispiel = Example Testing in the Gestagen Test in Infant Rabbits (McPhail Test) (d14)

[Key:]
Progesteron = Progesterone
mg/Tier/Tag = mg/animal/day
Vehikel = Vehicle
Beispiel = Example

PROGESTERONE RECEPTOR MODULATORS WITH INCREASED ANTIGONADOTROPIC ACTIVITY FOR FEMALE BIRTH CONTROL AND HORMONE REPLACEMENT THERAPY

This application claims the benefit of the filing date of U.S. Provisional Application Ser. No. 60/400,065 filed Aug. 2, 2002.

The invention relates to selective progesterone receptor modulators (SPRM) that can be used for treating gynecological disorders, especially for hormonal female contraception or in hormone replacement therapy.

Progesterone is secreted in large amounts from the ovary or the placenta during the cycle and in pregnancy. By interaction with estrogens, progesterone produces cyclic changes of the mucous membrane of the uterus in the menstrual cycle. In pregnancy, progesterone controls the relaxation of the myometrium and preserves the function of the decidual tissue.

Under the influence of elevated progesterone levels after ovulation, the mucous membrane of the uterus is converted into a state that allows the nidation of an embryo (blastocyst).

In a subtle way, progesterone is involved in the control of ovulation processes. It is known that progesterone has antiovulatory properties in connection with estrogens. The latter result from an inhibition of the hypophyseal gonadotropin secretion, which is a requirement for the maturation of a follicle and its ovulation. In contrast, it is evident that the comparatively low progesterone secretion of the maturing follicle plays an active role for the preparation and triggering of ovulation. In this connection, hypophyseal mechanisms (time-limited so-called positive feedback of progesterone on gonadotropin secretion) play a significant role (D. Loutradie, Human Reproduction 6, 1991, 1238-1240).

In addition, it is known that progesterone exerts a decisive influence on the endometrium. The endometrial proliferation is inhibited by the suppression of the estrogen-mediated mitosis in the uterus tissue (K. Chwalisz, R. M. Brenner, U. Fuhrmann, H. Hess-Stumpp, W. Elger, Steroids 65, 2000, 741-751).

Hormonal contraception can be considered as a combination that consists of antiovulatory strategy associated with the replacement of the deficient endogenic hormones. The conventional hormonal contraception consists in simulating the woman's natural cycle by a combination that consists of gestagens and estrogens by withdrawal bleeding being induced in a 28-day rhythm. Apart from its effectiveness, this method is distinguished by other advantages that can be seen in a reduction of the carcinogenic risk, especially ovarian or endometrial cancer, or its positive influence on the cardiovascular system.

A drawback of the conventional hormonal contraception is associated with the administration of relatively high doses of estrogens (i.a., ethinylestradiol, EE), which are essential for regular bleeding behavior. Estrogens, especially ethinylestradiol, significantly influence certain liver functions, such as, e.g., the synthesis of transport proteins CBG, SHBG, TBG, angiotensinogen, and in addition various functions that play a role in the physiology of blood-clotting as well as lipoproteins (HDL, LDL).

The strong estrogenic action of EE in the liver, but also the natural estrogens during pregnancy, are expressed, i.a., in an increased thromoembolic risk. Also, without the pathophysiological bases to recognize thromboembolic complications in particular, it can be assumed that, in this connection, hepatic estrogen actions have a decisive role.

Selective progesterone receptor modulators, also named mesoprogestins, are a new class of progesterone receptor (PR)-ligands, which show both an agonistic action and an antagonistic action on the progesterone receptor in vivo.

This results in a neutralization of the antiovulatory effectiveness that is present both in pure PR-agonists and in pure PR-antagonists [Slayden, O. D., Chwalisz, K., and Brenner, R. M. Reversible Suppression of Menstruation with Progesterone Antagonists in Rhesus Macaques. Hum Reprod 16: 1562-1574, 2001, Elger, W.; Bartley, J.; Schneider, B.; Kaufmann, G.; Schubert, G.; Chwalisz, K. Endocrine Pharmacological Characterization of Progesterone Antagonists and Progesterone Receptor Modulators with Respect to PR-Agonistic and Antagonistic Activity. Steroids 65, 713-723 (2000)]. Deficient or unreliable inhibitory effects on the ovulation bring up questions on antifertile effectiveness of corresponding mesoprogestins.

Another feature of the mesoprogestins is the reduced or deficient potential of the compounds to trigger an abortion compared to the compound RU 38 468 that acts almost exclusively as an antigestagen.

Chemical compounds of the structure shown below, in which R can be a hydrogen atom or an alkyl group and $R^1$ can be a hydrogen atom, an alkyl group or aryl group or an optionally substituted acyl function, are known as mesoprogestins:

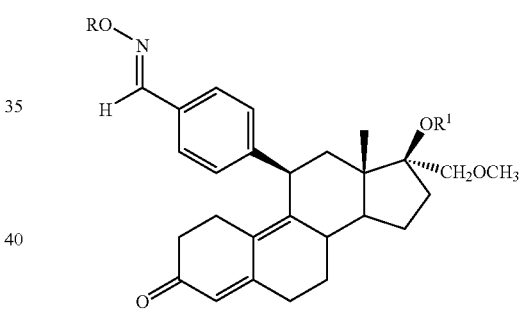

WO 01/44267 describes new 11β-phenylestradiene derivatives with fluoroalkyl groups in the aromatic side chain and production thereof. The compounds or the pharmaceutical preparations that contain these compounds are antihormonally effective and are therefore suitable for the treatment of diseases that are unfavorably influenced by cortisol or by corticoids, for the reduction of secreted cortisol, for stimulation of lactation, for treating dysmenorrhea and myomas, for treating Cushing's disease and for cervical maturation, for improving cognitive performance, for treating endometriosis or for hormone replacement therapy (HRT).

WO99/45023 relates to S-substituted 11β-benzaldoxim-estra-4,9-diene-carboxylic acid-thiol ester. The compounds have antigestagenic properties while at the same time having an antigluocorticoidal action that is significantly more reduced in comparison to that of RU 468.

In EP 909764, 11β-benzaldoxime-9α,10α-epoxy-estr-4-ene derivatives with high binding affinity to the progesterone receptor in the case of low glucocorticoid receptor affinity are described.

DE 4332283 and U.S. Pat. No. 5,693,628 relate to 11-benzaldoxim-estra-4,9-diene derivatives of general formula

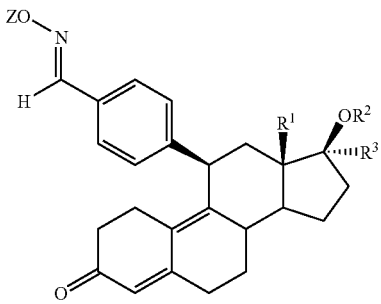

in which
R$^1$ is a hydrogen atom or an alkyl group,
R$^2$ is a hydrogen atom, an alkyl, aryl, aralkyl, or alkylaryl radical, a group CONHR$^4$ or CO$_2$R$^4$, in which R$^4$ can be a hydrogen atom, an alkyl, aryl, aralkyl or alkylaryl group with up to 10 carbon atoms,
R$^3$ is a hydrogen atom or an alkyl group, whereby the alkyl group can consist of 1-6 carbon atoms, or R$^3$ can mean a radical (CH$_2$)$_n$CH$_2$X with n=0, 1 or 2, and X can mean fluorine, chlorine, bromine or iodine, or cyano, azido or rhodano or a radical OR$^5$ or SR$^5$.

Z can mean both hydrogen and various other substituents.
The compounds 4-[17β-hydroxy-3-oxoestra-4,9-dien-11β-yl]benzaldehyde-1-(E)-oxime and 4-[17β-hydroxy-17α-methyl-3-oxoestra-4,9-dien-11β-yl]benzaldehyde-1-(E)-oxime are not mentioned explicitly.

The disclosed compounds are distinguished by a strong antigestagenic action with reduced glucocorticoidal activity.

In un-prepublished application DE 102 1034, 17α-fluoroalkyl-11β-benzaldoxime steroids of general formula

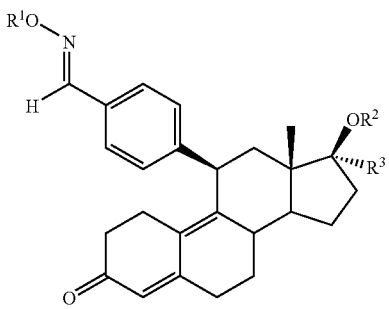

are described, in which
R$^1$ stands for hydrogen, C$_1$- to C$_6$-alkyl, COR$^4$, COOR$^4$, COSR$^4$ or CONHR$^5$, in which R$^4$ is C$_1$- to C$_6$-alkyl, or unsubstituted or substituted aryl, and in which R$^5$ is hydrogen, C$_1$- to C$_6$-alkyl or unsubstituted or substituted aryl,
R$^2$ stands for hydrogen, C$_1$- to C$_6$-alkyl or C$_1$- to C$_6$-acyl, and R$^3$ stands for a C$_n$F$_{2n+1}$ group, in which n=1, 2 or 3, or R$^3$ stands for a CH$_2$(CH$_2$)$_m$C$_n$F$_{2n+1}$, in which m=0 or 1, and n=1, 2 or 3, as antigestagenically active compounds with significantly reduced antiglucocorticoidal action in comparison to RU 38486.

The object of this invention is to make available compounds for female contraception that combine known advantages of conventional contraception and additional advantages. The contraceptive methods that can be carried out with the compounds according to the invention preferably will not require the addition of exogenous estrogens, however. In conventional contraceptives, the doses of EE used to achieve a reliable suppression of the ovarian function and to preserve a menstrual bleeding pattern are essential. The compounds according to the invention are to be distinguished by omitting or by reducing the dose of the estrogen components by a lower thromboembolic side-effect potential. It is to be possible to induce an amenorrhea by the compounds. At the same time, a stimulation of the mammary glands is to be avoided. Especially advantageous compounds are to be able to suppress both estrogenic and gestagenic effects in the endometrium. The compounds according to the invention are to inhibit the ovulation and to preserve the bone substance in the absence of estrogens; it is in the postmenopausal woman or is premenopausal after suppression of ovarian estrogen secretion.

The object is achieved according to this invention by the preparation of new 11β-benzaldoxime-estra-4,9-diene derivatives of general formula I

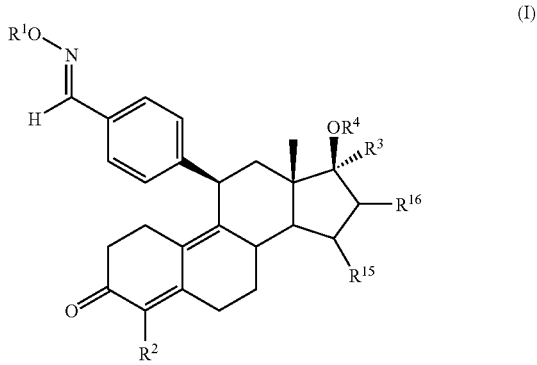

in which radicals R$^1$, R$^2$, R$^3$, R$^4$ and R$^5$ as well as R$^{15}$ and R$^{16}$ have the following meaning:
R$^1$ is a hydrogen atom, an alkanoyl radical with 1 to 10 carbon atoms or an optionally substituted benzoyl radical with 6-10 carbon atoms or a radical CONHR$^5$, whereby R$^5$ is a hydrogen atom, an alkyl or acyl radical with 1-10 carbon atoms in each case, or an alkylaryl or aralkyl radical with 6-10 carbon atoms in each case,
R$^2$ is a hydrogen atom, a halogen atom or a CF$_3$ group,
R$^3$ is a hydrogen atom or a group CH$_2$X, in which X stands for a hydrogen atom, a hydroxy group, a halogen atom, an alkyl radical with 1 or 2 carbon atoms, or X stands for a radical (CH$_2$)$_n$CH$_2$Y with n=0 or 1, and Y stands for a halogen atom,
whereby if
R$^2$ is a halogen atom, R$^3$ in addition can mean a group C$_n$F$_m$H$_o$, whereby n=1, 2, 3, 4 or 5, m>1 and m+o=n+1,
R$^4$ represents a hydrogen atom, an alkyl or alkanoyl radical that consists of 1-10 carbon atoms in each case or a benzoyl radical with 6-10 carbon atoms or a radical —CONHR$^5$, whereby R$^5$ has the above-indicated meaning,
R$^{15}$ and R$^{16}$ represent hydrogen atoms or together a double bond, whereby the compounds 4-[17α-chloromethyl-17β-hydroxy-3-oxoestra-4,9-dien-11β-yl]benzaldehyde-1-(E)-oxime and 4-[17α-chloromethyl-17β-methoxy-3-oxoestra-4,9-dien-11β-yl]benzaldehyde-1-(E)-oxime, already disclosed in DE 4332283 or U.S. Pat. No. 5,693,628, are excluded, as well as their pharmaceutically acceptable salts.

In addition, this invention comprises the new substances as pharmaceutical active ingredients, their production, their therapeutic use and the pharmaceutical dispensing forms that contain the new substances.

The compounds of general formula (I) according to the invention or their pharmaceutically acceptable salts can be used for the production of a pharmaceutical agent for use in female birth control as well as in female hormone replacement therapy (HRT).

For HRT, the compounds according to the invention can be used alone or associated with a natural estrogen (e.g., estradiol, its esters, estrone, estrone sulfate, estriol and prodrugs of these estrogens).

$R^2$ is preferably a chlorine atom or a bromine atom.

For substituents X and Y, a halogen atom can mean fluorine, chlorine or bromine.

If not defined in more detail, in terms of this invention, this is an aryl radical that optionally can be substituted by a phenyl radical or a 1- or 2-naphthyl radical, whereby the phenyl radical is preferred. If not expressly mentioned, aryl always also includes a heteroaryl radical. Examples of a heteroaryl radical are the 2-, 3- or 4-pyridinyl radical; the 2- or 3-furyl radical; the 2- or 3-thienyl radical; the 2- or 3-pyrrolyl radical; the 2-, 4- or 5-imidazolyl radical; the pyrazinyl radical; the 2-, 4- or 5-pyrimidinyl radical, or the 3- or 4-pyridazinyl radical.

Alkyl radicals are defined as straight-chain or branched-chain, saturated or unsaturated alkyl radicals. As representatives of straight-chain or branched-chain alkyl groups with 1-5 or 1-10 carbon atoms, for example, methyl, ethyl, propyl, isopropyl, butyl, isobutyl, tert-butyl, pentyl, isopentyl, neopentyl, heptyl, hexyl, and decyl can be mentioned; methyl, ethyl, propyl and isopropyl are preferred.

Preferred are compounds in which $R^1$ means a hydrogen atom, $R^2$ stands for a hydrogen atom, a chlorine atom or a bromine atom, and $R^3$ can be a hydrogen atom, a methyl group or a $CH_2X$ group, whereby X stands for a fluorine, chlorine or bromine atom, or a hydroxy group. Substituents $R^4$, $R^{15}$ and $R^{16}$ have the meaning that is indicated in general formula I.

Preferred are compounds in which $R^4$ is a hydrogen atom or an alkyl radical with 1 to 4 carbon atoms.

Especially preferred are:

4-[4'-Bromo-17β-hydroxy-3-oxoestra-4,9-dien-11β-yl]benzaldehyde-1-(E)-oxime,

4-[4'-Bromo-17β-hydroxy-17α-methyl-3-oxoestra-4,9-dien-11β-yl]benzaldehyde-1-(E)-oxime, 4-[4'-Bromo-17β-hydroxy-17α-trifluoromethyl-3-oxoestra-4,9-dien-11β-yl]benzaldehyde-1-(E)-oxime, 4-[17α-Bromomethyl-17β-hydroxy-3-oxoestra-4,9-dien-11β-yl]benzaldehyde-1-(E)-oxime, 4-[17β-Hydroxy-3-oxoestra-4,9-dien-11β-yl]benzaldehyde-1-(E)-oxime, 4-[17β-Acetoxy-3-oxoestra-4,9-dien-11β-yl]benzaldehyde-1-(E)-oxime, 4-[17β-Acetoxy-4'-bromo-3-oxoestra-4,9-dien-11β-yl]benzaldehyde-1-(E)-oxime, 4-[17β-Acetoxy-4'-bromo-3-oxoestra-4,9-dien-11β-yl]benzaldehyde-1-(E)-O-acetyl-oxime, 4-[17β-Benzoyloxy-3-oxoestra-4,9-dien-11β-yl]benzaldehyde-1-(E)-oxime, 4-[17β-(N-Ethylamino)carbonyloxy-3-oxoestra-4,9-dien-11β-yl]benzaldehyde-1-(E)-oxime, 4-[17β-Hydroxy-3-oxoestra-4,9-dien-11β-yl]benzaldehyde-1-(E)-[N-(ethylamino)-carbonyl]oxime, 4-[17β-Methoxy-3-oxoestra-4,9-dien-11β-yl]benzaldehyde-1-(E)-[N-(ethylamino)-carbonyl]oxime, 4-[17β-Methoxy-3-oxoestra-4,9-dien-11β-yl]benzaldehyde-1-(E)-oxime, 4-[4'-Bromo-17β-methoxy-3-oxoestra-4,9-dien-11β-yl]benzaldehyde-1-(E)-oxime, 4-[17β-Hydroxy-3-oxoestra-4,9,15-trien-11β-yl]benzaldehyde-1-(E)-oxime, 4-[17β-Methoxy-3-oxoestra-4,9,15-trien-11β-yl]benzaldehyde-1-(E)-oxime, 4-[17β-Hydroxy-17α-methyl-3-oxoestra-4,9-dien-11β-yl]benzaldehyde-1-(E)-oxime, 4-[4'-Chloro-17β-hydroxy-17α-trifluoromethyl-3-oxoestra-4,9-dien-11β-yl]benzaldehyde-1-(E)-oxime, 4-[4'-Chloro-17β-hydroxy-3-oxoestra-4,9-dien-11β-yl]benzaldehyde-1-(E)-oxime, 4-[17α-Fluoromethyl-17β-hydroxy-3-oxoestra-4,9-dien-11β-yl]benzaldehyde-1-(E)-oxime, 4-[4'-Bromo-17α-fluoromethyl-17β-hydroxy-3-oxoestra-4,9-dien-11β-yl]benzaldehyde-1-(E)-oxime, 4-[4'-Bromo-17α-chloromethyl-17β-hydroxy-3-oxoestra-4,9-dien-11β-yl]benzaldehyde-1-(E)-oxime, 4-[4'-Bromo-17α-bromomethyl-17β-hydroxy-3-oxoestra-4,9-dien-11β-yl]benzaldehyde-1-(E)-oxime, 4-[4'-Chloro-17β-methoxy-3-oxoestra-4,9-dien-11β-yl]benzaldehyde-1-(E)-oxime, 4-[4'-Chloro-17α-chloromethyl-17β-hydroxy-3-oxoestra-4,9-dien-11β-yl]benzaldehyde-1-(E)-oxime, 4-[17β-Ethoxy-3-oxoestra-4,9-dien-11β-yl]benzaldehyde-1-(E)-oxime, 4-[17β-Isopropyloxy-3-oxoestra-4,9-dien-11β-yl]benzaldehyde-1-(E)-oxime, 4-[17β-Benzyloxy-3-oxoestra-4,9-dien-11β-yl]benzaldehyde-1-(E)-oxime, 4-[17β-Methoxy-4'-trifluoromethyl-3-oxoestra-4,9-dien-11β-yl]benzaldehyde-1-(E)-oxime, 4-[4'-Chloro-17β-hydroxy-17α-methyl-3-oxoestra-4,9-dien-11β-yl]benzaldehyde-1(E)-oxime, 4-[17β-Hydroxy-17α-methyl-3-oxoestra-4,9-dien-11β-yl]benzaldehyde-1-(E)-[O-(ethylamino)carbonyl]oxime, 4-[17β-Hydroxy-17α-hydroxymethyl-3-oxoestra-4,9-dien-11β-yl]benzaldehyde-1-(E)-[O-(ethylamino)-carbonyl]oxime.

For the formation of pharmaceutically compatible salts of the compounds of general formula I according to the invention, i.a., hydrochloric acid, hydrobromic acid, sulfuric acid and phosphoric acid are considered as inorganic acids, and, i.a., acetic acid, propionic acid, maleic acid, fumaric acid, succinic acid, benzoic acid, ascorbic acid, oxalic acid, salicylic acid, tartaric acid, citric acid, lactic acid, malic acid, mandelic acid, cinnamic acid and methanesulfonic acid are considered as organic acids.

The compounds are distinguished by a mild androgenic and simultaneously improved antigonadotropic action. For the structurally closest compounds, as they are known from the above-mentioned prior art, no androgenic action was previously described. The substances of general formula I according to the invention represent compounds, moreover, that have an improved agonistic activity on the progesterone receptor compared to known compounds.

Biological Characterization of the Compounds According to the Invention

The substances of general formula I according to the invention were tested in the following models:

Receptor Binding Tests

Measurement of the Receptor Binding Affinity:

The receptor binding affinity was determined by competitive binding of a specifically binding $^3$H-labeled hormone (tracer) and the compound to be tested on receptors in the cytosol from animal target organs. In this case, receptor saturation and reaction equilibrium were sought.

The tracers and increasing concentrations of the compound to be tested (competitor) were co-incubated with the receptor-containing cytosol fraction at 0-4° C. over 18 hours. After separation of the unbonded tracer with carbon-dextran suspension, the receptor-bonded tracer portion was measured for each concentration, and the $IC_{50}$ was determined from the concentration sequence. As a quotient of the $IC_{50}$ values of the reference substance and the compound to be tested (×100%), the relative molar binding affinity (RBA) was calculated (RBA of the reference substance=100%).

For the individual receptor types, the following incubation conditions were selected:

Progesterone Receptor:

Uterus cytosol of the estradiol-primed rabbit; homogenized in TED buffer (20 mmol of Tris/HCl, pH 7.4; 1 mmol of ethylenediamine tetraacetate, 2 mmol of dithiothreitol) with 250 mmol of saccharose; stored at −30° C. Tracer: $^3$H-ORG 2058, 5 nmol; reference substance: progesterone.

Glucocorticoid Receptor:

Thymus cytosol of the adrenalectomized rat, thymi stored at −30° C.; buffer: TED. Tracer: $^3$H-Dexamethasone, 20 nmol; reference substance: dexamethasone.

Androgen Receptor:

Prostate cytosol of the castrated rat; prostates stored at −30° C.; buffer: TED with 10% glycerol as well as 2 μmol of triamcinolone acetonide. Tracer: $^3$H-metribolone 4 nmol; reference substances: metribolone (RU 1881) or 5α-dihydrotestosterone.

TABLE 1

| Ex. | $R_2$ | Oxime | 17β | 17α | PR[1] | GR[2] | AR[3] |
|---|---|---|---|---|---|---|---|
| 1 | H | H | OH | H | 26 | 3 | a) 17 b) 24 |
| 2 | H | H | OH | $CH_3$ | 95 | 12 | a) 16 b) 23 |
| 3 | H | H | $OCOCH_3$ | H | 20 | 12 | n.d. |
| 4 | H | H | OCONHEt | H | 13 | 11 | a) 2.9 b) 4.5 |
| 5 | H | H | $OCH_3$ | H | 159 | 14 | a) 21 b) 32 |
| 6 | Br | H | OH | $CH_3$ | 106 | 0.76 | a) 14 b) 22 |
| 7 | Br | H | $OCH_3$ | H | 110 | 0.69 | a) 8.7 b) 13.2 |
| 8 | Br | H | OH | $CF_3$ | 87 | 1.8 | a) 7.8 b) 11.8 |
| 9 | H | CONHEt | OH | $CH_3$ | 161 | 25 | a) 15 b) 23 |
| 10 | H | H | OH | $CH_2Br$ | 21 | 3 | a) 0.6 b) 0.9 |
| 11 | H | CONHEt | OH | H | 34 | 10 | a) 10 b) 15 |
| 12[4] | H | H | OH | H | 38 | 5 | a) 22 b) 34 |
| 13 | Br | H | $OCOCH_3$ | H | 45 | 0.35 | a) 6 b) 10 |
| 14 | Br | $COCH_3$ | $OCOCH_3$ | H | 23 | 0.3 | a) 6 b) 10 |
| 15 | H | H | $OC_2H_5$ | H | 143 | 17 | a) 13 b) 21 |
| 16 | H | H | OCOPh | H | 8 | 3 | a) 1.4 b) 2.2 |
| 17 | H | H | OPh | H | 31 | 8 | a) 2 b) 3 |
| 19 | Br | H | OH | H | 51 | 0.5 | a) 9 b) 16 |
| 20 | H | CONHEt | OH | $CH_2OH$ | 12 | 5 | a) 4 b) 7 |

[1] Progesterone = 100%,
[2] Dexamethasone = 100%,
[3] a) against RU 1881 (17β-hydroxy-17α-methyl-estra-4,9,11-trien-3-one) and b) against dihydrotestosterone (DHT), n.d. = not determined,
[4] additional 15,16-double bond.

Evaluation of Antifertile Effects of the Substances in the Perinidation Phase of Rats The determination of the progesterone-antagonistic activities was carried out on adult female rats in the nidation-inhibiting test.

The inhibition of the progesterone receptor leads to strong antifertile effects in the very early pregnancy of rats. Partial PR-agonistic properties of substances do not weaken the negative actions on pregnancy in this phase of the reproduction process (nidation) (Elger, W.; Bartley, J.; Schneider, B.; Kaufmann, G.; Schubert, G.; Chwalisz, K. Endocrine Pharmacological Characterization of Progesterone Antagonists and Progesterone Receptor Modulators with Respect to PR-Agonistic and Antagonistic Activity, Steroids 65, 713-723 (2000)). Unlike pure PR-antagonists, the substances according to the invention have no or have greatly reduced inhibiting effects on the pregnancy in terms of reduced or eliminated capacity to induce labor.

The principle of the test is described as follows: progesterone preserves pregnancy in all stages. An early-abortive action can accordingly be expected from competitive progesterone antagonists.

Female rats (Schoe strain: WIST Tierzucht GmbH Schönwalde) with a weight of 180-200 g were subjected daily to a cycle control and paired up in proestrus. The beginning of pregnancy was determined by detecting sperm in the vaginal smear on the same day (=day 1 of pregnancy=d1 p.c.).

From the $5^{th}$-$7^{th}$ day of pregnancy, the test substances were injected subcutaneously daily. On the $9^{th}$ day, vaginal smears were taken, then the animals were autopsied and the uteri were prepared.

The degeneration of implants and pathological, hemorrhagic and otherwise abnormal nidation sites were counted as abortions and are shown in Table 2.

TABLE 2

| Substance | Dosage Mg/Animal/Day | Rate of Animals with Complete Inhibition of Nidation |
|---|---|---|
| Vehicle Control | 0.2 ml of Benzyl Benzoate + Castor Oil (1 + 4) | 0/5 |

TABLE 2-continued

| Substance | Dosage Mg/Animal/Day | Rate of Animals with Complete Inhibition of Nidation |
|---|---|---|
| RU 38 486 | 0.3 | 0/5 |
| | 1.0 | 2/5 |
| | 3.0 | 5/5 |
| Example 1 | 1.0 | 0/5 |
| | 3.0 | 0/5 |
| | 10.0 | 5/5 |
| Example 2 | 0.03 | 0/4 |
| | 0.1 | 0/5 |
| | 0.3 | 2/5 |
| | 1.0 | 5/5 |
| Example 5 | 1.0 | 0/4 |
| Example 6 | 1.0 | 5/5 |

The results of these studies show that mesoprogestins according to the invention have PR-antagonistic properties.

Antiluteolysis Test/Ovulation-Inhibiting Test on Cyclic Guinea Pigs

Testing of the substances on progesterone-agonistic or progesterone-antagonistic activity was carried out in the antiluteolysis test on adult female guinea pigs after subcutaneous administration.

The principle of the test is represented as follows: The degeneration of the corpus luteum in the non-fertile cycle is carried out in guinea pigs by prostaglandins ($PGF_{2\alpha}$), which the uterus releases. In pregnancy, the corpora lutea persist since the embryo inhibits the prostaglandin secretion of the uterus [Elger, W.; Bartley, J.; Schneider, B.; Kaufmann, G.; Schubert, G.; Chwalisz, K. Endocrine Pharmacological Characterization of Progesterone Antagonists and Progesterone Receptor Modulators with Respect to PR-Agonistic and Antagonistic Activity. Steroids 65, 713-723 (2000)]. In the cycle, the progesterone stimulates the secretion of $PGF2\alpha$ of the uterus. Pure PR antagonists inhibit this function completely (inhibition of luteolysis). This test arrangement makes it possible to detect the inhibition of the uterine prostaglandin release as an antiluteolytic action by progesterone content determinations in the serum between days d0; d6/d7/d8 and d10-d18. At the same time, the ovulation inhibition can be determined by histological evaluation of the corpora lutea in the ovary (new corpora lutea=ovulation).

Female guinea pigs (Schoe strain: DH, Tierzucht GmbH Schönwalde) with a weight of 500 g were subcutaneously treated from day 10 to day 17 daily with test substances or comparison substances onapristone and RU 486 in the dose of 10 mg/animal/day. The substance vehicle benzyl benzoate/castor oil was administered to the control group. The administration volume was 0.2 ml/animal/day, and each group included 5 test animals.

Figure 1:
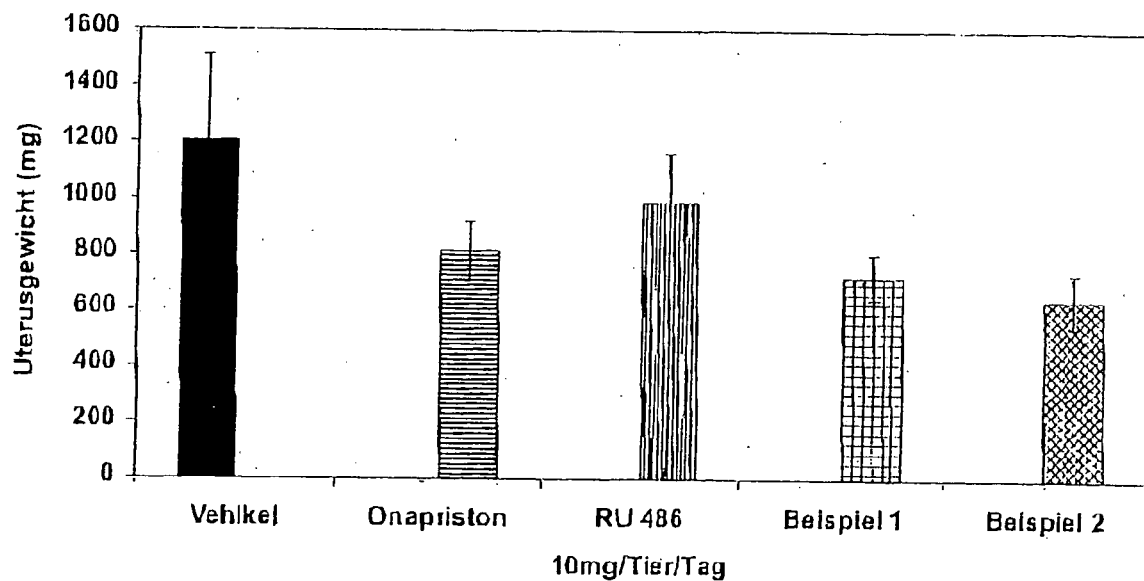
FIGS. 1 and 2 show the results of testing for inhibition of uterine prostaglandin release as antiluteolytic action by progesterone content determinations in the serum.
Figure 2:
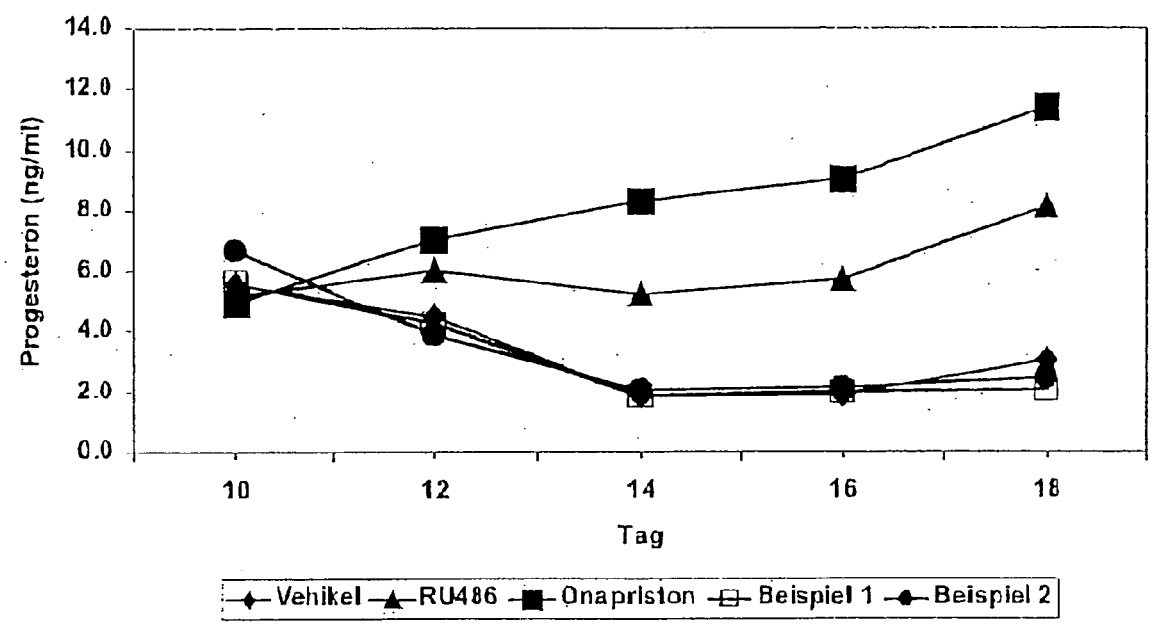
Figure 3:
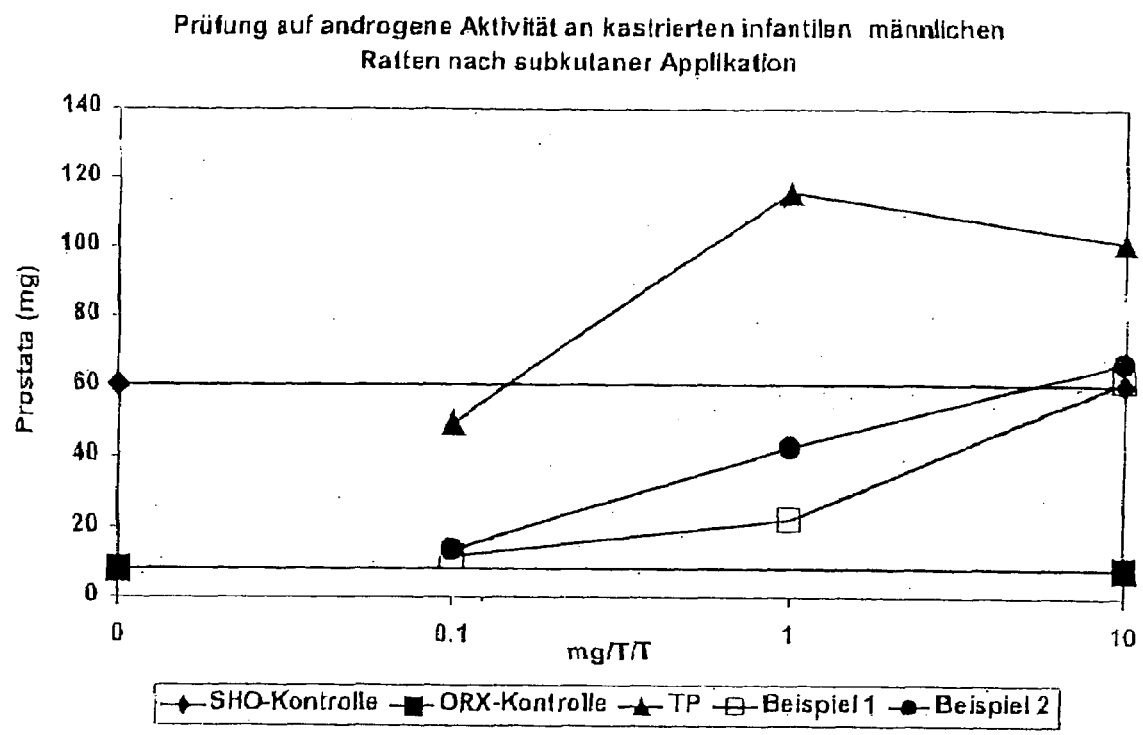
FIGS. 3-6 show the results of testing for AR-agonistic and LH/FSH-reducing action.
Figure 4:
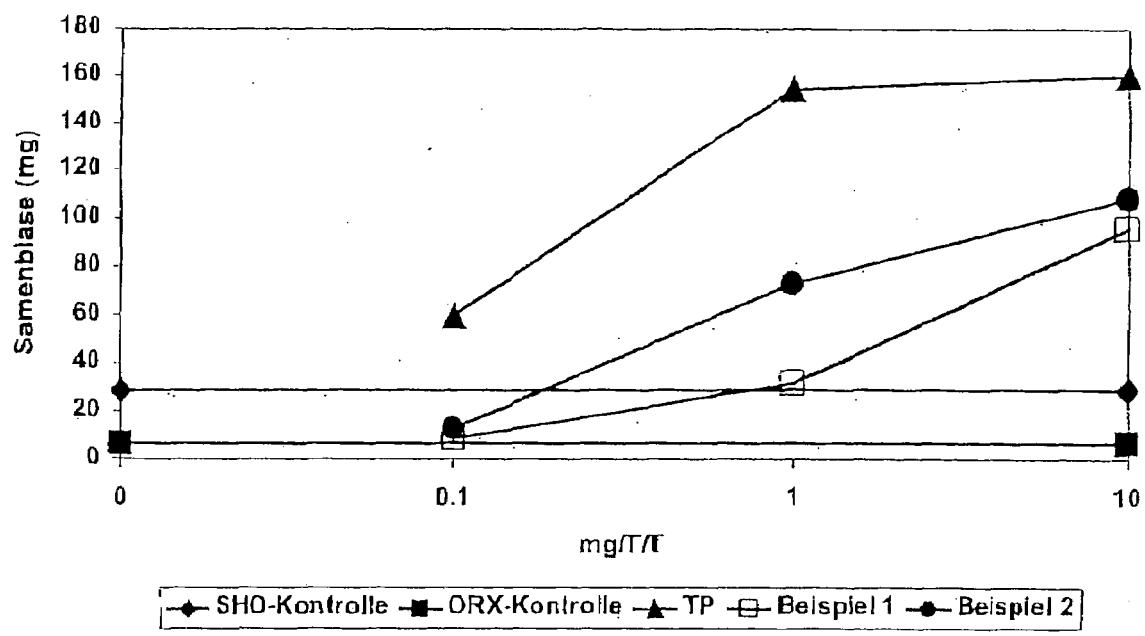
Figure 5:
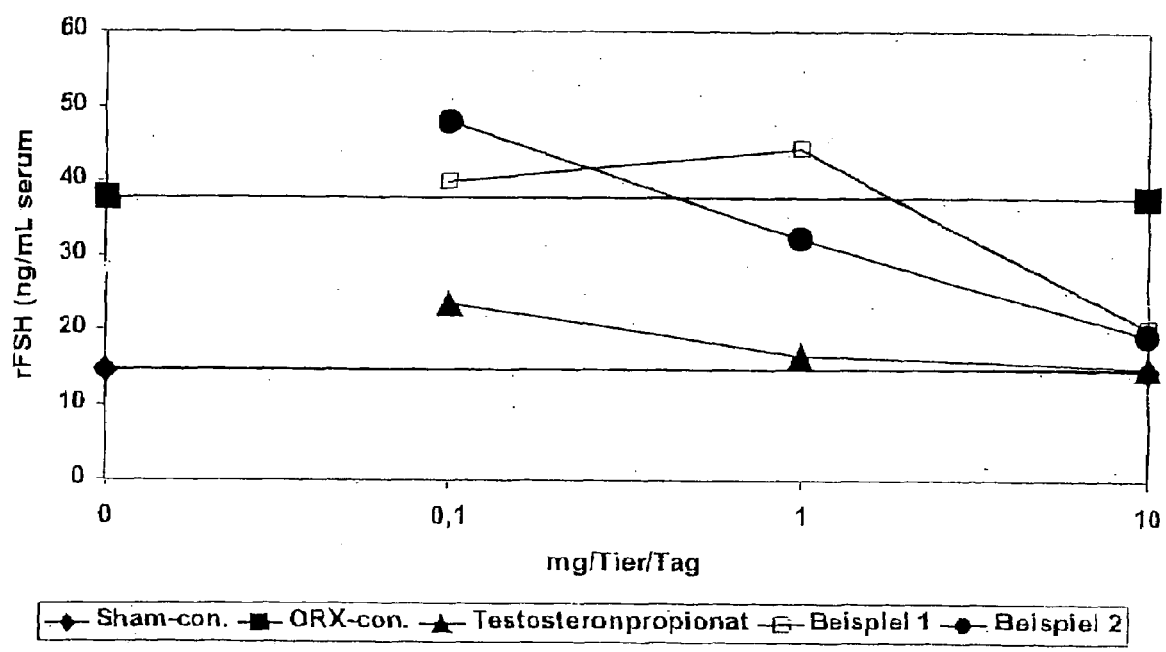
Figure 6:
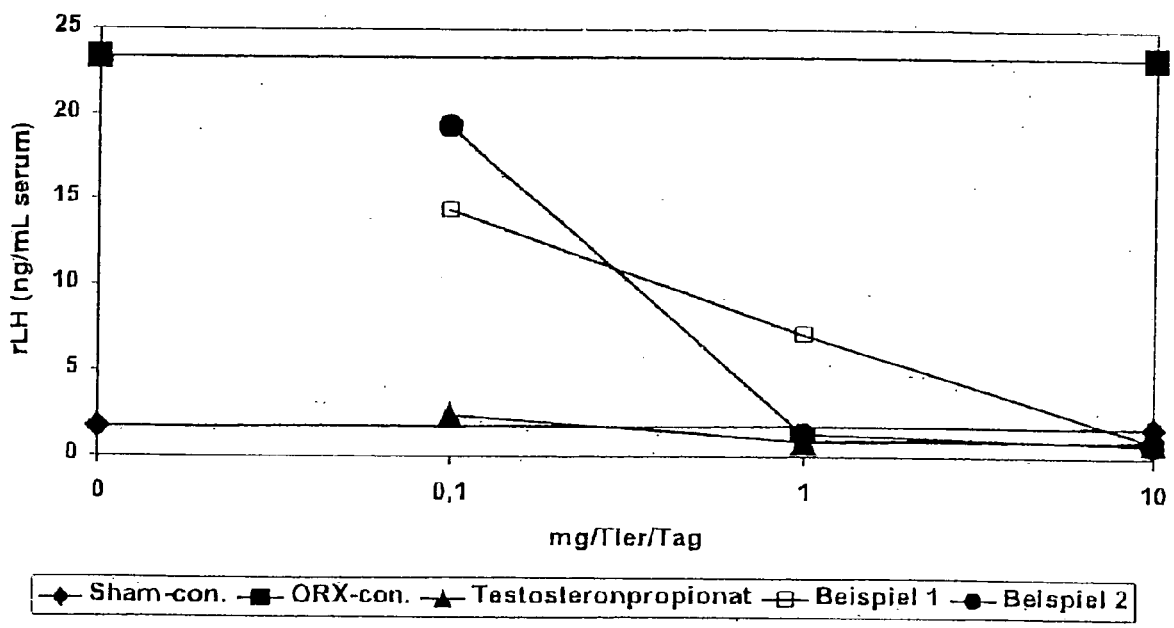

On days 10, 12, 14, 16 and 18, blood samples were taken from the postorbital venous plexus to determine progesterone content. 24 hours after the last administration, the animals were autopsied. The results are shown in FIGS. 1 and 2.

Substances with affinity to PR and AR that inhibit the ovulation but not the degeneration of the corpora lutea are mesoprogestins according to the invention.

Determination of the Androgenic and Antigonadotropic Properties of the Substances in the Hershberger Test on Infantile Rats The determination of the androgenic properties was carried out in the Hershberger test on infant male rats after subcutaneous administration over 7 days.

The principle of the test is represented as follows: the function and size of the accessory sexual glands (seminal vesicles and prostates) and the Musculus levator ani depend on the presence of androgens. A castration consequently results in the atrophy of these organs. If, after castration, an androgen (testosterone propionate) is substituted, the increase in the weight of the accessory glands can be considered to indicate that substances exert an androgenic activity.

Male infant animals (Mol strain: WIST, Tierzucht GmbH Schönwalde) with a weight of 40-50 g underwent orchiectomies (ORX). A control group remained uncastrated but underwent a sham operation (SHO). The vehicle of the test substances benzyl benzoate/castor oil was administered to control groups ORX and SHO (n/group=10 animals).

Testosterone propionate (standard) and the test substances were subcutaneously administered in the doses 0.1; 1.0 and 10 mg/animal/day, administration volumes 0.2 ml/animal/day.

24 hours after the $7^{th}$ administration, the animals were autopsied. The results are shown in FIGS. 3, 4, 5 and 6.

Substances with an AR-agonistic and LH/FSH-reducing action in this assay and PR-agonistic and antagonistic properties are mesoprogestins according to the invention.

Determination of the Estrogenic and Osteoprotective Action of the Substances on Adult Rats The tests on estrogenic and osteoprotective activity after subcutaneous administration over 28 days was carried out on female, 6-month-old rats (Shoe strain: WIST, Tierzucht GmbH Schönwalde). The animals were ovariectomized and equipped with osmotic pumps (Alzet) for continuous subcutaneous administration of test substances. The animals were autopsied on day 29.

Figure 7:
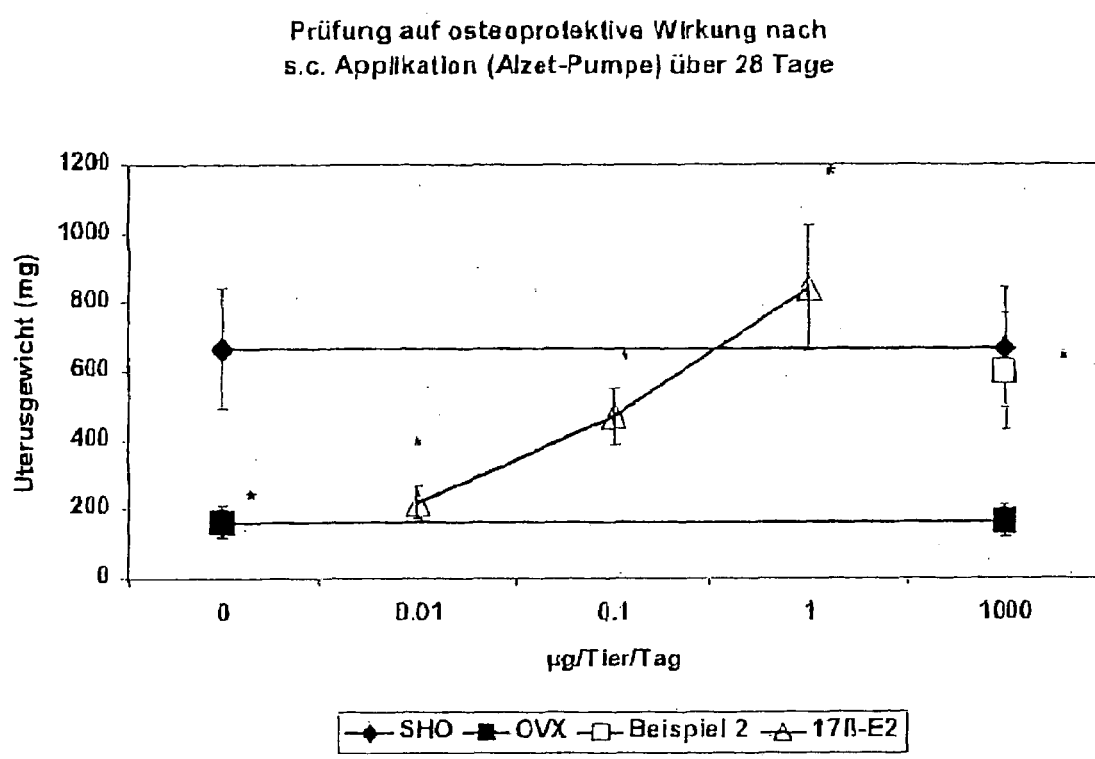
FIGS. 7 and 8 demonstrate the osteoprotective action of the compounds of the invention.
Figure 8:
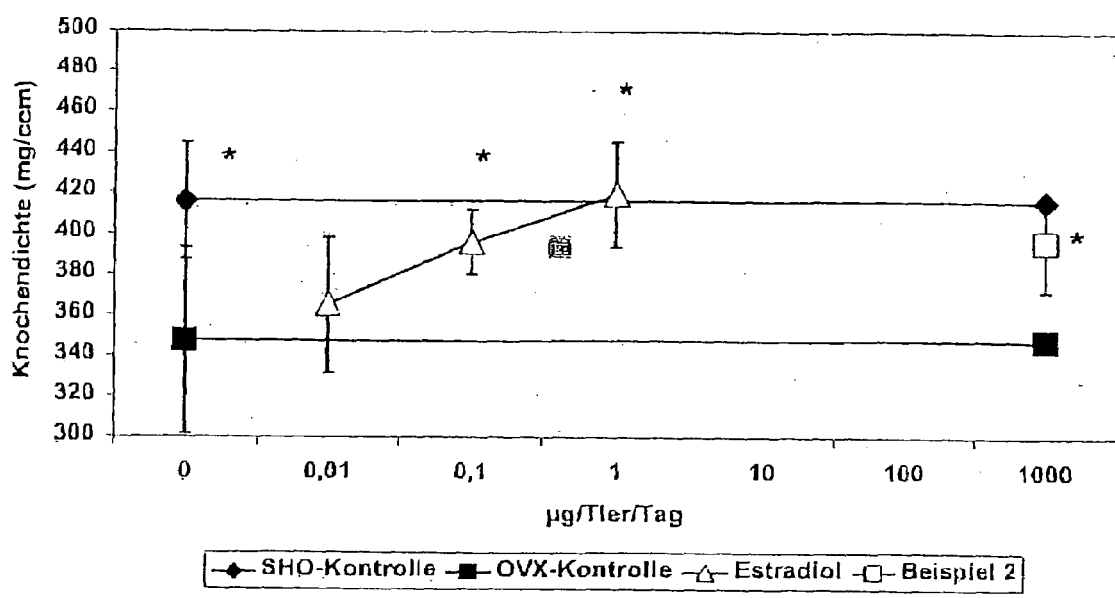

To determine the estrogenic properties of substances, the uterus weight was determined. The bone density was determined by means of QCT (quantitative computer tomography) on the prepared tibia. The results are shown in FIGS. 7 and 8.

The results of these studies show that substances according to the invention have an osteoprotective action per se.

Determination of the Gestagenic Action of the Substances

Tests on gestagenic and antigestagenic activity were carried out on infant rabbits in the McPhail test.

The principle is represented as follows: by interaction of estrogens and progesterone, the endometrium is prepared for the implantation of the fertilized ovocytes. In this case, this results in completely characteristic changes in the endometrium, which can be clearly detected in rabbits. Estrogens produce a proliferation. The action of gestagens sets in only once the endometrium is proliferated. Gestagens produce a so-called transformatory conversion of the endometrium.

Infant rabbits (New Zealand white. Supplier: Harlan Winkelmann) with a weight of 700-900 g received 17β-estradiolbenzoate (5 µg/animal/day in 0.2 ml, s.c.) once daily as priming over 6 days (d1-d6). On test day d7, the administration of the test substances as well as the comparison substances progesterone and RU 486 began once daily over 7 days subcutaneously in benzyl benzoate/castor oil. A control group received one vehicle administration daily (benzyl benzoate/castor oil).

On day d14, the test was completed. First, blood samples were taken and then autopsies were carried out.

The replication of secretory structures of the endometrium typical of the gestagenic action is evaluated in the histological preparations according to the McPhail scale (stage 1-4; 0=no action, 4=full action).

Figure 9:
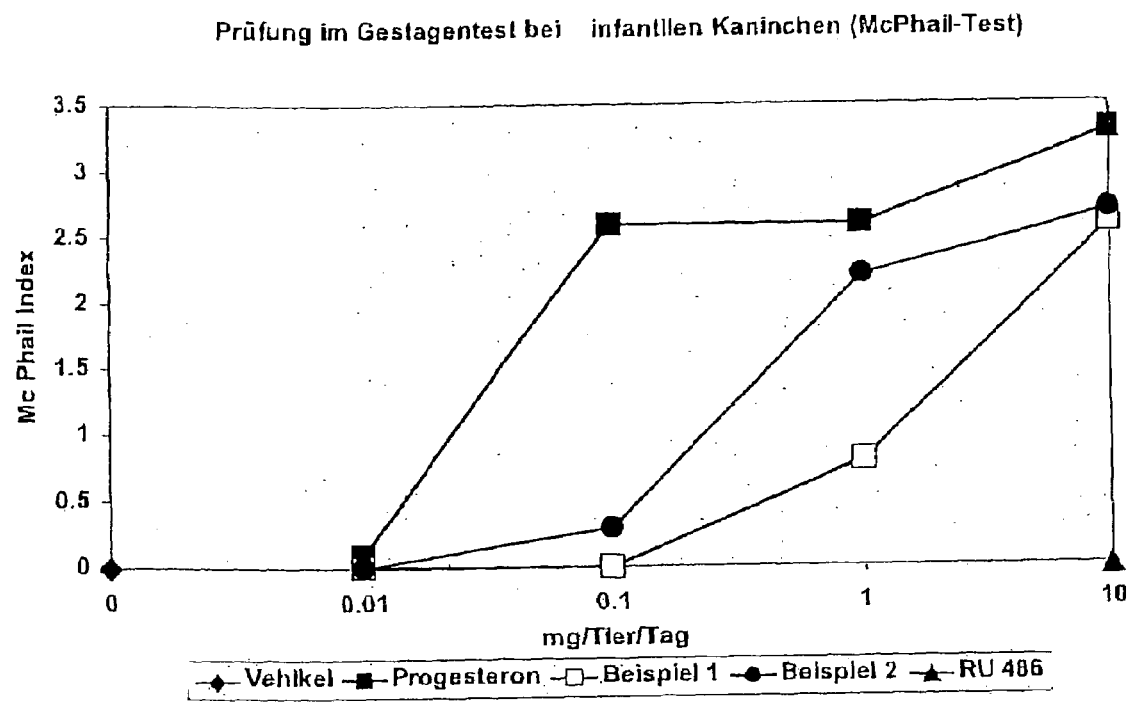
FIGS. 9-11 show the gestagenic and antigestagenic action of the compound of the invention.
Figure 10:
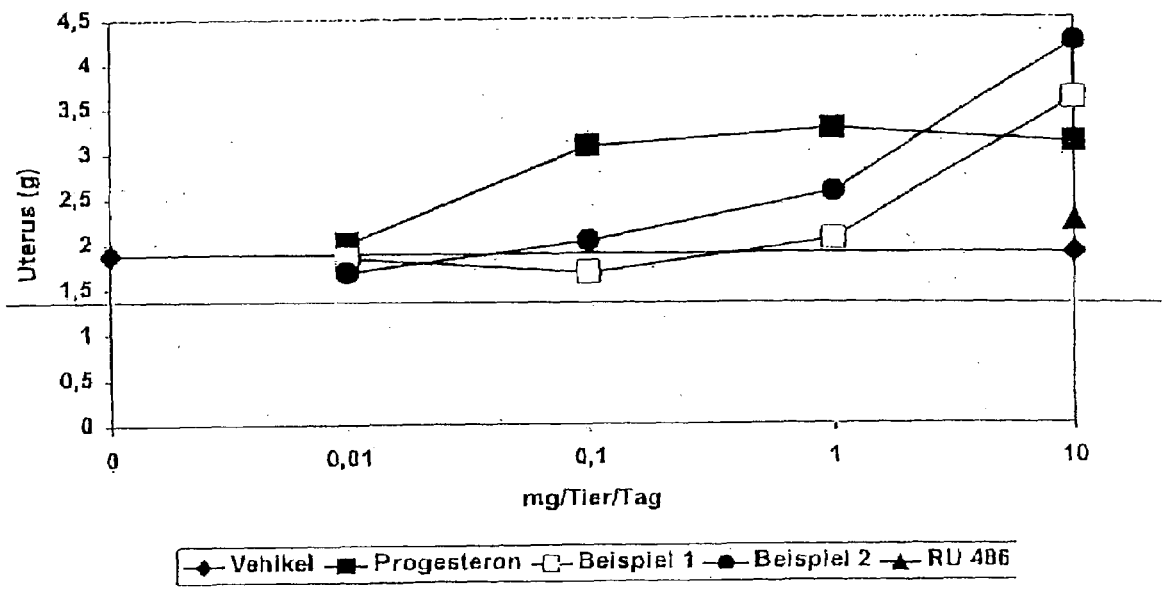
Figure 11:
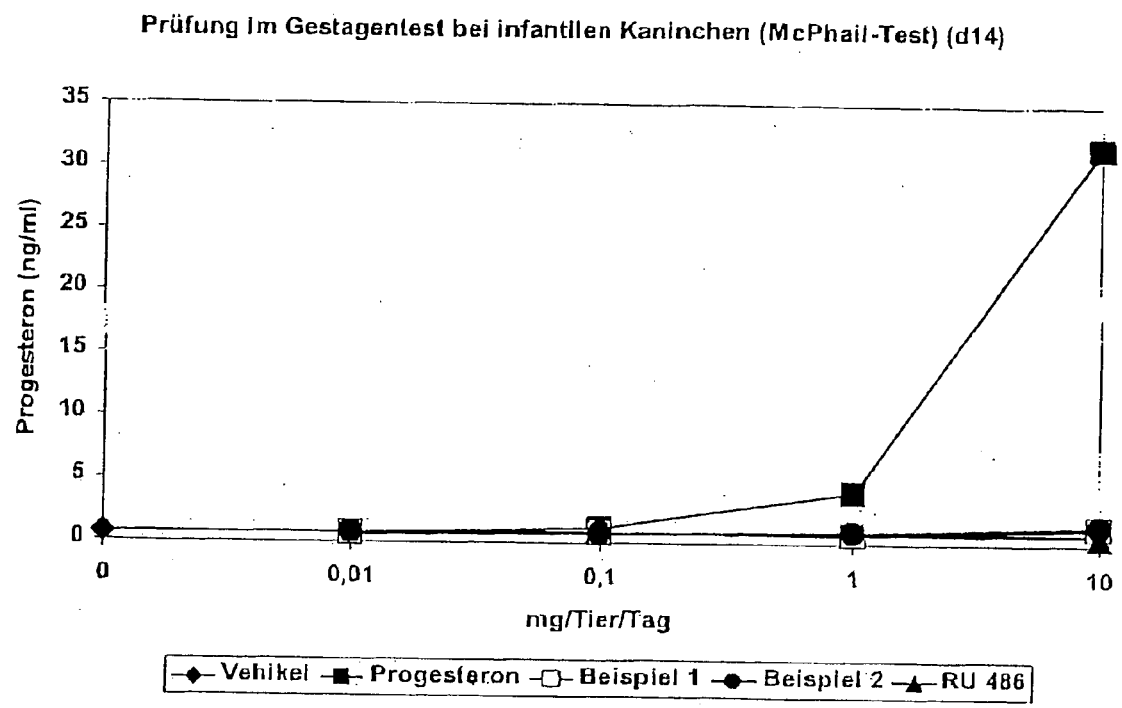

The results are shown in FIGS. 9, 10, and 11.

Substances with an AR-agonistic action that weaken the action of progesterone in this assay but themselves trigger submaximal progesterone-analogous effects in the endometrium are mesoprogestins according to the invention.

Pharmaceutical Preparations and Indications

The compounds of general formula I represent a new type of mesoprogestins with both agonistic action on the progesterone receptor and improved antigonadotropic and mild androgenic action after peroral administration. As a result, previously impossible forms of hormone treatment are being developed.

This invention comprises the new substances as pharmaceutical active ingredients, their production, their therapeutic application and the pharmaceutical dispensing forms that contain the new substances.

The new mesoprogestins that are described here or their pharmaceutically acceptable salts can be used both without estrogens and with the addition of low-dose natural estrogens such as estradiol or their esters for the production of pharmaceutical agents that can be used in female birth control, in female hormone replacement therapy and for the treatment of gynecological diseases such as endometriosis, uterus myomatoses, dysfunctional bleeding and dysmenorrhea. In this connection, the estrogens can also be used in the form of their sulfamates. For the production and the special pharmacological properties of the sulfamates, see J. Steroid Biochem. Molec. Biol, 55, 395-403 (1995); Exp. Opinion Invest. Drugs 7, 575-589 (1998).

The new progesterone receptor modulators are suitable by their high antiovulatory activity for a preferably estrogen-free or estrogen-dose-reduced contraception in women. The bleeding control is taken over by the mesoprogestin/gestagen components of the compounds according to the invention in contrast to conventional contraceptive agents. The purpose of the treatment is to induce an amenorrhea. The estrogen component in these preparations has the task of avoiding an estrogen deficit. As a result, the compounds according to the invention must not be combined with EE, but rather can preferably be added without estrogens or in combination with small doses of natural estrogens (e.g., estradiol, its esters, estrone, estrone sulfate, estriol and prodrugs of these estrogens).

By the natural cycle or under the hormonal contraception with a combined contraceptive agent (estrogen and gestagen treatment), a constant rise and fall of the female hormone condition is created. A significant increase in the risk of developing breast cancer, ovarian or endometrial carcinoma may be associated therewith [Coutinho, E. M. and Segal, S. *Is Menstruation Obsolete?*, Oxford University Press (1999)]. Classic gestagens stimulate the breast tissue of women [Isaksson, E.; von Schoultz, E.; Odlind, V., et al. Effects of Oral Contraceptives on Breast Epithelial Proliferation. *Breast Cancer Res Treat* 65: 163-169 (2001)].

The spectrum of hormonal properties of the substances according to the invention inhibits, however, the proliferation in the breast. Androgens have a significantly inhibiting effect on the proliferation of the mammary glands. Accordingly, the substances according to the invention have special advantages in this respect.

The use of the substances according to the invention for the production of pharmaceutical agents for use as a contraceptive agent thus makes possible a completely new concept of contraception, in which the risk of breast cancer is significantly limited.

In addition, in premenopausal women, the condition of a reversible amenorrhea can develop without the negative signs of an estrogen deficiency, since a basal estrogen secretion is also often maintained in the case of inhibited ovulation based on the dose. An estrogen-free or estrogen-dose-reduced contraception method in turn results in that the known side effects, such as thromboembolic complications, can be significantly reduced.

The substances according to the invention or their pharmaceutically compatible salts can also be used as single components. The use of low-dose, preferably natural estrogens, such as estradiol and its esters, results in a relaxation of the ovaries and the endometrium, which contributes to a reduction of undesirable proliferation appearances in the above-mentioned tissues.

Compared to conventional hormonal HRT products, the absence of any bleeding is an important feature. In addition, the advantageous effect of ovarian androgens on the CNS and metabolic functions is substituted by the substances according to the invention via their androgenic activity. Unlike gestagens, the compounds according to the invention do not stimulate the glandular tissue of the breast.

The special advantage of the compounds according to the invention relative to the treatment of gynecological diseases such as endometriosis, uterus myomatoses, dysfunctional bleeding and dysmenorrhea lies in their elevated antifertile action in comparison to compounds that do not have any androgenic activity. By the increased antiovulatory activity of the compounds according to the invention, pregnancies under the treatment of gynecological diseases with mesoprogestins are ruled out.

The compounds of general formula I according to the invention and their acid addition salts are suitable for the production of pharmaceutical compositions and preparations. The pharmaceutical compositions or pharmaceutical agents contain as active ingredients at least one or more of the compounds of general formula I according to the invention or their acid addition salts, optionally in combination with other pharmacologically active substances. The production of the pharmaceutical agent is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmann's Enzyklopädie der technischen Chemie [Ullmann's Encyclopedia of Technical Chemistry], 4, 1953, 1-39; J. Pharm. Sciences, 52, 1963, 918 ff; issued by Czetsch-Lindenwald, Hilfsstoffe für Pharmazie und angrenzende Gebiete [Adjuvants for Pharmaceutics and Related Fields]; Pharm Ind. 2, 1961, 72 ff; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G. Aulendorf in Württemberg 1971.

The formulation of the pharmaceutical preparations based on the new compounds is carried out in a way that is known in the art, in that the active ingredient is processed with the vehicles, fillers, substances that influence decomposition, binding agents, moisturizers, lubricants, absorbents, diluents, flavoring correctives, dyes, etc., that are commonly used in galenicals and converted into the desired form of administration. In this case, reference is made to Remington's Pharmaceutical Science, 15$^{th}$ Ed. Mack Publishing Company, East Pennsylvania (1980).

The preferred preparations consist in a dispensing form that is suitable for oral administration. Those dispensing forms are, for example, tablets, film tablets, coated tablets, capsules, pills, powders, solutions or suspensions or else depot forms.

The compounds of the general formula according to the invention or the pharmaceutical compositions that contain at least one of the compounds according to the invention are preferably administered orally.

Corresponding tablets can be obtained, for example, by mixing active ingredient with known adjuvants, for example inert diluents such as dextrose, sugar, sorbitol, mannitol, polyvinyl pyrrolidone, explosives such as corn starch or alginic acid, binding agents such as starch or gelatin, lubricants such as magnesium stearate or talc, and/or agents for achieving a depot effect, such as carboxylpolymethylene, carboxyl methyl cellulose, cellulose acetate phthalate or polyvinyl acetate. The tablets can also consist of several layers.

Coated tablets can accordingly be produced by coating cores, which are produced analogously to the tablets, with agents that are commonly used in tablet coatings, for example polyvinyl pyrrolidone or shellac, gum arabic, talc, titanium oxide or sugar. In this case, the shell of the coated tablet can also consist of several layers, whereby the adjuvants that are mentioned above in the tablets can be used.

Solutions or suspensions with the compounds of general formula I according to the invention can contain in addition flavor-improving agents such as saccharin, cyclamate or sugar, as well as, e.g., flavoring substances such as vanilla or orange extract.

In addition, they can contain suspending adjuvants such as sodium carboxymethyl cellulose, or preservatives, such as p-hydroxy-benzoates.

The capsules that contain compounds of general formula I can be produced, for example, by the compound of general formula I being mixed with an inert vehicle such as lactose or sorbitol and encapsulated in gelatin capsules.

Dosage

The amount of the compounds to be administered fluctuates within a wide range and can cover any effective amount.

Based on the effect to be achieved and the type of administration, the amount of compound to be administered can encompass a range of 0.01 to 50 mg. In humans, a recommended daily dose lies in the range of 0.05 to 10 mg.

Suitable dosages for the compounds according to the invention are from 0.1 to 10 mg.

The compounds according to the invention are administered continuously, preferably daily to once weekly.

The compounds according to the invention are suitable for vaginal, intrauterine and subcutaneous administrations in suitable vehicle systems (elastomers). From case to case, this dispensing form allows lower dosages than those indicated above.

The invention also comprises the compounds of general formula I according to the invention as therapeutic active ingredients together with pharmaceutically compatible and acceptable adjuvants and/or vehicles.

The invention also comprises pharmaceutical compositions that contain one of the pharmaceutically active compounds according to the invention or a mixture of the latter or a pharmaceutically compatible salt as well as pharmaceutically compatible adjuvants and vehicles.

The compounds of general formula I according to the invention can be produced as described below:

Access to the 11β-benzaldoxime-estra-4,9-diene derivatives of general formula I according to the invention is carried out via the 3,3-dimethoxy-estra-5(10),9(11)-dien-17-one [Pierdet, A.; Vignau, M. FR 5183 (1966)], which is converted with $H_2O_2$ in the presence of hexafluoroacetone into 3,3-dimethoxy-5α,10α-epoxiestr-9(11)-en-17-one [Costerousse, G.; Teutsch, G.; EP 5100 (1979); Teutsch, G.; Ojasoo, T.; Raynaud, J. P.: J. Steroid Biochem. 31, 1988, 549-565]. The introduction of the 11β-benzaldehyde grouping is carried out by Grignard reaction with the corresponding bromobenzaldehyde acetal. After functionalization at C-17, the 11β-benzaldehyde acetal is hydrolyzed and then oximized (see formula diagram 1):

Formelschema 1

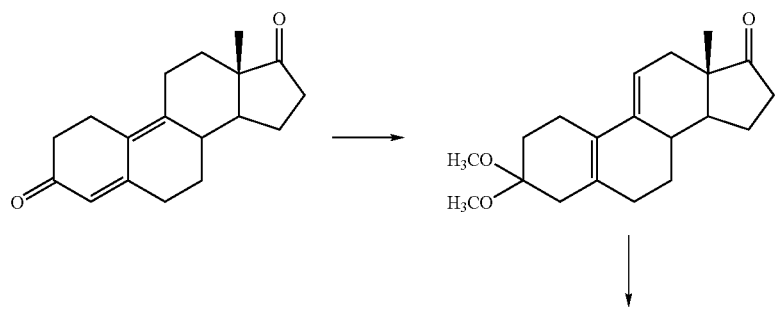

-continued

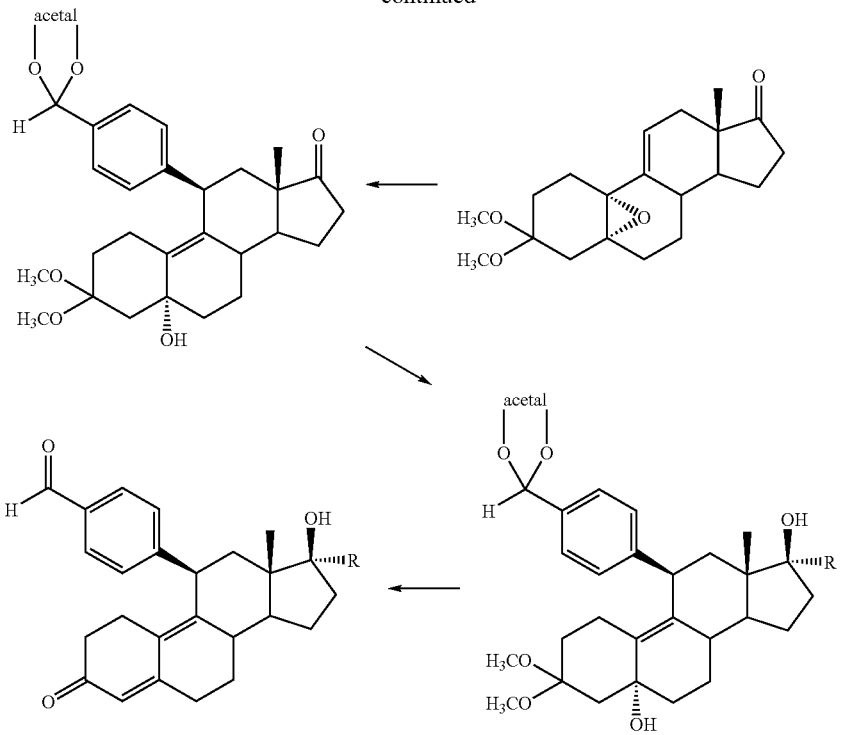

[Formula Diagram 1]

The introduction of substituents $R_2$ to C-4 is carried out according to standard methods in each case after the introduction of the benzaldehyde group. The chlorine substituent is introduced with N-chlorosuccinimide into tetrahydrofuran, and the same is done with bromine with N-bromosuccinimide. The C-4 substitution with a $CF_3$ group is performed as described by Fei et al. (X. S. J. Fei et al., Chem. Soc. Perkin Trans 1, 1998, 1139-1142).

The examples below are used for a more detailed explanation of the invention without it being limited thereto:

EXAMPLE 1

4-(17β-Hydroxy-3-oxoestra-4,9-dien-11β-yl)benzaldehyde-1(E)-oxime 115 mg of 4-(17β-hydroxy-3-oxoestra-4,9-dien-11β-yl) benzaldehyde is dissolved in 2 ml of pyridine and reacted in portions with 23 mg of hydroxylaminohydrochloride at 23° C. After 2 hours, it is diluted with ice water, the precipitate is suctioned off, washed with water and dried. 100 mg of 4-(17β-hydroxy-3-oxoestra-4,9-dien-11β-yl)benzaldehyde-1(E)-oxime, which is purified by preparative layer chromatography on silica gel $PF_{254+366}$ with toluene/acetone 4:1 and recrystallized from ethyl acetate, is obtained.

Melting point: 150 to 153° C. (ethyl acetate)

$\alpha_D = +280°$ ($CHCl_3$)

$^1$H-NMR spectrum in $CDCl_3$ [δ, ppm] 0.42 (s, 3H, H-18), 3.68 (t, 1H, H-17α), 4.38 (d, J=6.9 Hz, 1H, H-11α), 5.79 (s, 1H, H-4), 7.21 and 7.49 (m, 4H, A,A', B,B'-system of aromatic compound protons), 7.78 (s, 1H, NOH), 8.11 (s, 1H, CH=N—).

Production of the Starting Compound

Step 1

426 mg of CuCl is added to a Grignard solution (produced from 1.6 g of magnesium and 17.7 g of 4-bromo-benzaldehyde neopentylketal in 100 ml of THF) at −20° C., it is stirred for 10 minutes, and 5 g of 3,3-dimethoxy-5α,10α-epoxy-estr-9-en-17-one in 25 ml of anhydrous THF is added in drops. At 0° C., it is stirred for 1.5 more hours and decomposed with aqueous ammonium chloride solution. After ethyl acetate is added, the phases are separated. The organic phase is washed with aqueous ammonium chloride solution and water, dried on sodium sulfate and concentrated by evaporation under reduced pressure. The light-colored syrup is purified on silica gel with a toluene/ethyl acetate gradient. 3.24 g of a crude product is obtained. By recrystallization from tert-butyl methyl ether/n-hexane, 3,3-dimethoxy-11β-[4-(5,5-dimethyl-1,3-dioxan-2-yl)phenyl]-5α-hydroxy-estr-9-en-17-one is isolated as colorless crystals.

Melting point: 194 to 202° C. (tert-butyl methyl ether/n-hexane)

$\alpha_D = +64°$ ($CHCl_3$)

$^1$H-NMR spectrum in $CDCl_3$ [δ, ppm] 0.46 (s, 3H, H-18), 0.80 and 1.31 (2s; 3H, 2×$CH_3$ each), 3.20 and 3.33 (2; 3H, $OCH_3$ each), 3.63-3.79 (m, 4H, $CH_2$), 4.30 (d, J=6.9 Hz, 1H, H-11α), 4.66 (s, 1H, OH), 5.35 (s, 1H, PhH ketal), 7.24 and 7.41 (2d, 4 H, A,A', B,B'-system of the aromatic compound protons).

Step 2

2.1 g of 3,3-dimethoxy-11β-[4-(5,5-dimethyl-1,3-dioxan-2-yl)phenyl]-5α-hydroxy-estr-9-en-17-one is dissolved in 25 ml of methanol/THF (1:1, V/V) and reduced at 23° C. with 303 mg of sodium borohydride. After 45 minutes, it is stirred into water, and the aqueous phase is extracted several times with methylene chloride. The organic phase is dried and evaporated under reduced pressure. The crude product [4-(3, 3-dimethoxy-5α,17β-dihydroxy-estr-9-en-11β-yl)benzaldehyde-neopentylketal] is dissolved in 25 ml of acetone, and stirred with 2 ml of water and 283 mg of p-toluenesulfonic acid at room temperature for 8 hours. Then, it is poured into water and the precipitate is suctioned off. The purification of the crude product is carried out by chromatography with a toluene/acetone gradient on silica gel. 1.1 g of 4-(17β-hydroxy-3-oxoestra-4,9-dien-11β-yl)benzaldehyde is obtained.

Melting point: 197 to 200° C. (acetone)

$\alpha_D$=+225° ($CHCl_3$)

$^1$H-NMR spectrum in $CDCl_3$ [δ, ppm] 0.40 (s, 3H, H-18), 3.68 (t, 1H, J=9.0 Hz, H-17α), 4.44 (d, J=7.2 Hz, 1H, H-11α), 5.80 (s, 1H, H-4); 7.38 (d, 2H, J=8.1 Hz, aromatic compound protons), 7.81 (d, 2H, J=6.6 Hz, aromatic compound protons), 9.98 (s, 1H, CH=O).

EXAMPLE 2

4-(17β-Hydroxy-17α-methyl-3-oxoestra-4,9-dien-11β-yl)benzaldehyde-1(E)-oxime 428 mg of 4-(17β-hydroxy-17α-methyl-3-oxoestra-4,9-dien-11β-yl)benzaldehyde is reacted according to Example 1 in pyridine with 148 mg of hydroxylamino-hydrochloride at 23° C. The crude product is purified by preparative layer chromatography on silica gel $PF_{254+366}$ with toluene/acetone 4:1 and recrystallized from tert-butyl methyl ether.

Melting point: 154 to 160° C. [tert-butyl methyl ether]

$\alpha_D$=+224° ($CHCl_3$)

$^1$H-NMR spectrum in $CDCl_3$ [δ, ppm] 0.53 (s, 3H, H-18), 1.27 (s, 3H, 17α-$CH_3$), 4.42 (d, J=6.9 Hz, 1H, H-11α), 5.79 (s, 1H, H-4), 7.22 and 7.50 (m, 4 H, A,A', B,B'-system of the aromatic compound protons), 7.79 (s, 1H, NOH), 8.11 (s, 1H, CH=N—).

Production of the Starting Compound

The 11β-benzaldehyde ethylene acetal group is introduced from 3,3-dimethoxy-5α,10α-epoxy-estr-9-en-17-one with 4-bromobenzaldehyde-ethylene acetal via Grignard according to Example 1, step 1. Then, the crude product in THF is added in drops to a Grignard solution (produced from 2.43 g of magnesium and 6.4 ml of methyl iodide in 25 ml of tert-butyl methyl ether). After 2 hours, the Grignard solution is decomposed with aqueous ammonium chloride solution, and the 4-(3,3-dimethoxy-5α,17β-dihydroxy-17α-methy-estr-9-en-11β-yl)benzaldehyde-ethylene acetal is isolated by extraction after common working-up.

The crude product is dissolved in 15 ml of acetone, mixed with 0.5 ml of water and 150 mg of p-toluenesulfonic acid and hydrolyzed according to Example 1 to 4-(17β-hydroxy-17α-methyl-3-oxoestra-4,9-dien-11β-yl)benzaldehyde and purified by chromatography.

Melting point: 160 to 164° C. (acetone)

$\alpha_D$=+211° ($CHCl_3$);

$^1$H-NMR spectrum in $CDCl_3$ [δ, ppm] 0.50 (s, 3H, H-18), 1.28 (s, 3H, 17α-$CH_3$), 4.48 (d, J=7.2 Hz, 1H, H-11α), 5.80 (s, 1H, H-4), 7.38 (d, 2H, J=8.1 Hz, aromatic compound protons), 7.81 (d, 2H, J=6.6 Hz, aromatic compound protons), 9.98 (s, 1H, CH=O).

EXAMPLE 3

4-(17β-Acetoxy-3-oxoestra-4,9-dien-11β-yl)benzaldehyde-1-(E)-oxime 450 mg of 4-(17β-acetoxy-3-oxoestra-4,9-dien-11β-yl)benzaldehyde is reacted in pyridine with 75 mg of hydroxylaminohydrochloride according to Example 1. The crude product is purified by preparative layer chromatography on silica gel $PF_{254+366}$ and recrystallized from acetone.

Melting point: 130 to 135° C. (acetone)

$\alpha_D$=+204° ($CHCl_3$)

$^1$H-NMR spectrum in $CDCl_3$ [δ, ppm] 0.47 (s, 3H, H-18), 2.03 (s, 3H, $COCH_3$), 4.35 (d, J=6.9 Hz, 1H, H-11α), 4.63 (t, 1H, H-17α), 5.79 (s, 1H, H-4), 7.21, 7.50 (2d, 4 H, A,A', B,B'-system of the aromatic compound protons); 7.64 (s, 1H, NOH), 8.11 (s, 1H, CH=N—)

Production of the Starting Compound 437 mg of 4-(17β-hydroxy-3-oxoestra-4,9-dien-11β-yl)benzaldehyde is acetylated with 6 ml of acetic anhydride/pyridine 1:1 at room temperature within 3 hours. By adding ice water, a crude product is precipitated, which is purified by recrystallization from acetone. 226 mg of 4-(17β-acetoxy-3-oxoestra-4,9-dien-11β-yl)benzaldehyde is obtained.

Melting point: 188 to 191° C. (acetone)

$\alpha_D$=+202° ($CHCl_3$);

$^1$H-NMR spectrum in $CDCl_3$ [δ, ppm]: 0.44 (s, 3H, H-18), 2.04 (s, 3H, $COCH_3$), 4.40 (d, J=6.9 Hz, 1H, H-11α), 4.63 (t, 1H, J=8.1 Hz, H-17α), 5.80 (s, 1H, H-4), 7.37 (d, 2H, J=8.1 Hz, aromatic compound protons), 7.80 (d, 2H, J=8.1 Hz, aromatic compound protons), 9.98 (s, 1H, CH=O).

EXAMPLE 4

4-[17β-(N-Ethylamino)carbonyloxy-3-oxoestra-4,9-dien-11β-yl]benzaldehyde-1(E)-oxime 500 mg of 4-[17β-(N-ethylamino)carbonyloxy-3-oxoestra-4,9-dien-11β-yl]benzaldehyde is reacted with hydroxylaminohydrochloride in pyridine according to Example 1 and purified by chromatography. 318 mg is obtained as a colorless foam from acetone.

$\alpha_D$=+218° ($CHCl_3$)

$^1$H-NMR spectrum in $CDCl_3$ [δ, ppm]: 0.43 (s, 3H, H-18), 1.15 (t, 3H, J=7.2 Hz, $CH_2CH_3$), 3.23 (t, J=6.6 Hz, 17α H), 4.35 (d, 1H, J=7.2 Hz, H-11α), 4.6 (m, $NHCH_2$), 5.79 (s, 1H, H-4), 7.21 (d, 2H, J=7.8 Hz, aromatic compound protons), 7.50 (d, 2H, J=7.8 Hz, aromatic compound protons), 7.9 (s, 1H, NOH), 8.11 (s, 1H, CH=N).

Production of the Starting Compound 870 mg of 4-(17β-hydroxy-3-oxoestra-4,9-dien-11β-yl)benzaldehyde (Example 1) is refluxed in 30 ml of toluene with 2.4 ml of ethyl isocyanate for 8 hours. It is cooled, 6 ml of aqueous $NH_3$ is added, it is stirred for 1 hour at room temperature and extracted several times with $CH_2Cl_2$. The organic phase is washed neutral, dried on $Na_2SO_4$, and the residue is vacuum-evaporated and purified by chromatography. 530 mg of 4-[17β-(N-ethylamino)-carbonyloxy-3-oxoestra-4,9-dien-11βyl]benzaldehyde is obtained as a light-colored foam that is incorporated directly into the oximization.

$^1$H-NMR spectrum in $CDCl_3$ [δ, ppm]: 0.41 (s, 3H, H-18), 1.14, 1.18 (2t, 3H, J=7.2, 7.8 Hz, $CH_2CH_3$), 3.22 (t, J=6.6 Hz, 17αH), 4.41 (d, 1H, J=7.8 Hz, H-11α), 4.59 (t, J=7.8 Hz, $NHCH_2$), 5.80 (s, 1H, H-4), 7.37 (d, 2H, J=8.1 Hz, aromatic compound protons), 7.81 (d, 2H, J=8.1 Hz, aromatic compound protons), 9.98 (s, 1H, CH=O).

EXAMPLE 5

4-(17β-Methoxy-3-oxoestra-4,9-dien-11β-yl)benzaldehyde-1(E)-oxime

Analogously to Example 1, from 4-(17β-methoxy-3-oxoestra-4,9-dien-11β-yl)benzaldehyde and hydroxylaminohydrochloride in pyridine.

Melting point: 111 to 113° C. (acetone)
$\alpha_D$=+262° (CHCl$_3$);
$^1$H-NMR spectrum in CDCl$_3$ [δ, ppm]: 0.43 (s, 3H, H-18), 3.25 (t, 1H, J=8.0 Hz, 17α-H), 3.34 (s, 3H, OCH$_3$), 4.35 (d, J=7.2 Hz, 1H, H-11α), 5.78 (s, 1H, H-4), 7.20 (d, 2H, J=8.8 Hz aromatic compound protons), 7.48 (d, 2H, J=8.4 Hz, aromatic compound protons), 8.09 (s, 1H, CH=N—).

Production of the Starting Compound

An 11β-benzaldehyde-dimethylacetal grouping is introduced from 3,3-dimethoxy-5α,10α-epoxy-estr-9-en-17-one with 4-bromobenzaldehyde-diemethylacetyl via Grignard, according to Example 1, step 1, and then the 17-keto group is reduced with sodium borohydride according to Example 1.

5.26 g of 4-(3,3-dimethoxy-5α,17β-dihydroxy-estr-9-en-11β-yl)benzaldehyde-dimethylacetal is dissolved in 50 ml of toluene, and mixed with 3.37 g of potassium tert-butanolate and then with 1.9 ml of methyl iodide. After 4 hours, it is diluted with water, and the organic phase is washed neutral with aqueous ammonium chloride solution and water, dried on sodium sulfate and concentrated by evaporation under vacuum.

The yellow oil of 4-(5α-hydroxy-3,3,17β-trimethoxy-estr-9-en-11β-yl)benzaldehyde-dimethylacetal is dissolved in 50 ml of acetone, mixed with 650 mg of p-toluenesulfonic acid and stirred for 12 hours at room temperature. It is poured into 0.4 l of ice water, whereby 4-(17β-methoxy-3-oxoestra-4,9-dien-11β-yl)benzaldehyde precipitates as a colorless product that is suctioned off and washed neutral. After purification by column chromatography on silica gel, a crude product is obtained, which is recrystallized from acetone.

Melting point: 133 to 135° C. (acetone)
$\alpha_D$=+244° (CHCl$_3$);
$^1$H-NMR spectrum in CDCl$_3$ [δ, ppm]: 0.40 (s, 3H, H-18), 3.25 (t, 1H, J=8.0 Hz, 17α-H), 3.33 (s, 3H, OCH$_3$), 4.41 (d, J=7.2 Hz, 1H, H-11α), 5.78 (s, 1H, H-4), 7.37 (d, 2H, J=8.0 Hz aromatic compound protons), 7.79 (d, 2H, J=8.4 Hz, aromatic compound protons), 9.96 (s, 1H, CH=O).

EXAMPLE 6

4-(4'-Bromo-17β-hydroxy-17α-methyl-3-oxoestra-4,9-dien-11β-yl)benzaldehyde-1(E)-oxime Analogously to Example 1, from 4-(4'-bromo-17β-hydroxy-17α-methyl-3-oxoestra-4,9-dien-11β-yl)benzaldehyde and hydroxylaminohydrochloride in pyridine.

Melting point: 157° C. (decomposition, ether)
$\alpha_D$=+175° (CHCl$_3$)
$^1$H-NMR spectrum in CDCl$_3$ [δ, ppm] 0.53 (s, 3H, H-18), 1.25 (s, 3H, 17α-CH$_3$), 4.41 (d, J=7.2 Hz, 1H, H-11α), 7.17 and 7.47 (2d, 4H, J=8.0 Hz, A,A', B,B'-system of the aromatic compound protons), 8.08 (s, 1H, CH=N—).

Production of the Starting Compound 781 mg of 4-(17β-hydroxy-17α-methyl-3-oxoestra-4,9-dien-11β-yl)benzaldehyde is dissolved in 25 ml of tetrahydrofuran and mixed with 356 mg of N-bromosuccinimide. The mixture is stirred for 2 hours at room temperature, then poured into 200 ml of ice water. The precipitate is filtered off, washed neutral and dried. After purification by means of preparative layer chromatography, 475 mg of 4-(4'-bromo-17β-hydroxy-17α-methyl-3-oxoestra-4,9-dien-11β-yl)benzaldehyde is obtained as a foam, which is incorporated directly into the oximization analogously to Example 1 with hydroxylammonium hydrochloride in pyridine.

$^1$H-NMR spectrum in CDCl$_3$ [δ, ppm]: 0.52 (s, 3H, H-18), 1.27 (s, 3H, 17α-CH$_3$), 3.21 (2t, 1H, OH), 4.41 (d, J=7.2 Hz, 1H, H-11α), 7.34 and 7.79 (2d, 4H, J=8.0 Hz, A,A', B,B'-system of the aromatic compound protons), 9.96 (s, 1H, CH=O).

EXAMPLE 7

4-(4'-Bromo-17β-methoxy-3-oxoestra-4,9-dien-11β-yl)benzaldehyde-1(E)-oxime

Production analogously to Example 1 from 4-(4'-bromo-17β-methoxy-3-oxoestra-4,9-dien-11β-yl)benzaldehyde with hydroxylaminohydrochloride in pyridine.

Melting point: 145° decomposition (tert-butyl methyl ether)
$\alpha_D$=+198° (CHCl$_3$)
$^1$H-NMR spectrum in CDCl$_3$ [δ, ppm]: 0.44 (s, 3H, H-18), 3.26 (t, 1H, H-17α), 3.34 (s, 3H, OCH$_3$), 4.34 (d, J=7.6 Hz, 1H, H-11α), 7.17 and 7.47 (2d, 4H, J=8 Hz, A,A', B,B'-system of the aromatic compound protons), 8.08 (s, 2H, =NOH and CH=N—).

Production of the Starting Compound

Analogously to Example 6 from 4-(17β-methoxy-3-oxoestra-4,9-dien-11β-yl)benzaldehyde with N-bromosuccinimide in THF, pale yellow foam that is incorporated directly into the oximization.

$^1$H-NMR spectrum in CDCl$_3$ [δ, ppm] 0.42 (s, 3H, H-18), 3.26 (t, 1H, H-17α), 3.33 (s, 3H, OCH$_3$), 4.40 (d, J=7.2 Hz, 1H, H-11α), 7.34 and 7.79 (2d, 4H, J=8 Hz, A,A', B,B'-system of the aromatic compound protons), 9.96 (s, 1H, CH=O).

EXAMPLE 8

4-(4'-Bromo-17β-hydroxy-17α-trifluoromethyl-3-oxoestra-4,9-dien-11β-yl)benzaldehyde-1(E)-oxime Production analogously to Example 1 from 4-(4'-bromo-17β-hydroxy-17α-trifluoromethyl-3-oxoestra-4,9-dien-11β-yl)benzaldehyde and hydroxylamino-hydrochloride in pyridine.

Melting point: 198 to 203° C. (ether, n-hexane)
$\alpha_D$=+154° (CHCl$_3$)
$^1$H-NMR spectrum in CDCl$_3$ [δ, ppm]: 0.60 (s, 3H, H-18), 3.22 (2t, 1H, OH), 4.44 (d, J=7.2 Hz, 1H, H-11α), 7.17 and 7.48 (2d, 4H, J=8.0 and 8.8 Hz, A,A', B,B'-system of the aromatic compound protons), 7.88 (s, 1H, NOH), 8.09 (s, 1H, CH=N—).

Production of the Starting Compounds 4-(4'-Bromo-17β-hydroxy-17α-trifluoromethyl-3-oxoestra-4,9-dien-11β-yl)benzaldehyde Analogously to Example 6 from 4-(17β-hydroxy-17α-trifluoromethyl-3-oxoestra-4,9-dien-11β-yl)benzaldehyde with N-bromosuccinimide in THF, light yellow foam that is incorporated directly into the oximization.

$^1$H-NMR spectrum in CDCl$_3$ [δ, ppm]: 0.59 (s, 3H, H-18), 3.22 (2t, 1H, OH), 4.50 (d, J=7.6 Hz, 1H, H-11α), 7.35 and 7.80 (2d, 4H, J=8.4 Hz, A,A', B,B'-system of aromatic compound protons), 9.96 (s, 1H, CH=O).

4-[17β-Hydroxy-17α-(1,1,1-trifluoromethyl)-3-oxoestra-4,9-dien-11β-yl]benzaldehyde 1 g of 3,3-Dimethoxy-11β-{[4-(1,1-ethylenedioxy)methyl]phenyl}5α-hydroxy-estr-9-en-17-one is dissolved in 30 ml of absolute THF, mixed with 1.0 g of molecular sieve 3A and stirred for 30 minutes under argon. It is cooled to 0° C., 1.5 ml of trifluoromethyltrimethylsilane is added in drops, it is stirred for another 10 minutes, and then 1 g of tetrabutylammonium fluoride is added. After 10 at 5° C., the reaction solution is decomposed by adding 10 ml of 1 N HCl. It is allowed to come to room temperature, 100 ml of water and ethyl acetate are added in each case, the phases are separated, the organic phase is washed neutral, dried on sodium sulfate, the organic phase is filtered off and concentrated by evaporation under vacuum. After acetone is added, 1.05 g of yellow crystals remains. Recrystallization from acetone and treatment with tert-butyl methyl ether yields 480 mg of 4-[17β-hydroxy-17α-(1,1,1-trifluoromethyl)-3-oxoestra-4,9-dien-11β-yl]benzaldehyde.

Melting point: 284 to 292° C. (acetone)

$α_D$=+221° (CHCl$_3$)

$^1$H-NMR spectrum in CDCl$_3$: [δ, ppm]: 0.58 (s, 3H, H-18), 4.51 (d, 1H, J=7.1 Hz, H-11α), 5.81 (s, 1H, H-4), 7.38 (d, 2H, J=8.3 Hz, aromatic compound protons), 7.81 (d, 2H, J=8.3 Hz), 9.97 (s, 1H, CH=O).

EXAMPLE 9

4-[17β-Hydroxy-17α-methyl-3-oxoestra-4,9-dien-11β-yl]benzaldehyde-1-(E)-[O-(ethylamino)-carbonyl]oxime Analogously to Example 4 from 4-(17β-hydroxy-17α-methyl-3-oxoestra-4,9-dien-11β-yl)-benzaldehyde-1(E)-oxime with ethyl isocyanate in toluene.

Melting point: 178 to 183° C. (acetone/n-hexane)

$α_D$=+264° (CHCl$_3$)

$^1$H-NMR spectrum in CDCl$_3$ [δ, ppm]: 0.52 (s, 3H, H-18), 1.24 (t, 3H, CH$_2$CH$_3$), 1.62 (s, 3H, CH$_3$), 3.38 (m, 2H, CH$_2$), 4.45 (d, J=7.2 Hz, 1H, H-11α), 5.80 (s, 1H, H-4), 6.24 (t, 1H, NH), 7.28 (d, 2H, J=8.4 Hz, aromatic compound protons), 7.59 (d, 2H, J=8.1 Hz, aromatic compound protons), 8.30 (s, 1H, CH=N—).

EXAMPLE 10

4-(17α-Bromomethyl-17β-hydroxy-3-oxoestra-4,9-dien-11β-yl)benzaldehyde-1(E)-oxime Production analogously to Example 1 from 4-(17α-bromomethyl-17β-hydroxy-3-oxoestra-4,9-dien-11β-yl)benzaldehyde with hydroxylamine in pyridine.

Melting point: 107 to 109° C. (acetone)

$α_D$=+161° (CHCl$_3$)

$^1$H-NMR spectrum in CDCl$_3$ [δ, ppm]: 0.63 (s, 3H, H-18), 3.60 (d, 2H, J=10.4 Hz, CH$_2$), 3.79 (d, 2H, J=9.6 Hz, CH$_2$), 4.42 (d, J=7.2 Hz, 1H, H-11α), 5.80 (s, 1H, H-4), 7.18 and 7.48 (2d, 4 H, J=8.4 Hz, A,A', B,B'-system of the aromatic compound protons), 8.09 (s, 1H, CH=N—), 8.27 (s, 1H, NOH).

LC/MS: 484.0 (M$^+$+H)

Production of the Starting Compound 5 mmol of 4-(3,3-dimethoxy-5α-hydroxy-17-oxoestr-9-en-11β-yl)benzaldehyde-ethylene acetal is reacted according to Corey, E. J., Chaykowsky, J. (J. Am. Chem. Soc. 1962, 84, 3782) in DMF with 10 mmol of trimethylsulfonium iodide and 10 mmol of potassium-tert-butanolate at room temperature within 3 hours to form spiroepoxide. 1.98 g of 4-(3,3-dimethoxy-5α-hydroxy-17(S)-spiroepoxy-estr-9-en-11β-yl) benzaldehyde-ethylene acetal is dissolved in 30 ml of dimethylformamide and cooled to about 0° C. After 5 ml of hydrobromic acid is added, it is stirred for 10 more minutes at 0° C., and then the batch is allowed to come to room temperature. After 1 hour, the reaction mixture is stirred into 400 ml of aqueous sodium bicarbonate solution, whereby a pale yellow precipitate is deposited, which is suctioned off, washed neutral and dried. 1.69 g of 4-(17α-bromomethyl-17β-hydroxy-3-oxoestra-4,9-dien-11β-yl)benzaldehyde is obtained, which is purified by chromatography. A colorless foam that is incorporated directly into the oximization is obtained.

LC/MS: 469.0 (M$^+$+H).

$^1$H-NMR spectrum in CDCl$_3$ [δ, ppm]: 0.61 (s, 3H, H-18), 2.33 (s, 1H, OH), 3.60 and 3.78 (2d, 2H, J=10.4 Hz and J=10.0 Hz, CH$_2$), 4.49 (d, J=6.8 Hz, 1H, H-11α), 5.80 (s, 1H, H-4), 7.36 and 7.80 (2d, 4H, J=8.0 Hz, A,A', B,B'-system of the aromatic compound protons), 9.96 (s, 1H, CH=O).

EXAMPLE 11

4-[17β-Hydroxy-3-oxoestra-4,9-dien-11β-yl]benzaldehyde-1-(E)-[O-(ethylamino)-carbonyl]oxime Analogously to Example 4 from 4-(17β-hydroxy-3-oxoestra-4,9-dien-11β-yl)benzaldehyde-1(E)-oxime with 3 equivalents of ethylisocyanate in toluene/acetone mixture (3:1).

Melting point: starting from 127° C. decomposition (ethyl acetate)

$α_D$=+263° (CHCl$_3$)

$^1$H-NMR spectrum in CDCl$_3$ [δ, ppm]: 0.42 (s, 3H, H-18), 1.24 (t, 3H, CH$_2$CH$_3$), 1.74 (s, 1H, OH), 3.68 (t, 1H, H-17α), 4.11 (q, 2H, ΣJ=21.6 Hz, CH$_2$Me), 4.40 (d, J=6.8 Hz, 1H, H-11α), 5.78 (s, 1H, H-4), 6.24 (t, 1H, NH), 7.27 (d, 2H, J=8.4 Hz, aromatic compound protons), 7.59 (d, 2H, J=8.1 Hz, aromatic compound protons), 8.29 (s, 1H, CH=N—).

EXAMPLE 12

4-(17β-Hydroxy-3-oxoestra-4,9,15-trien-11β-yl)benzaldehyde-1(E)-oxime

Analogously to Example 1 from the 4-(17β-hydroxy-3-oxoestra-4,9,15-trien-11β-yl)benzaldehyde with hydroxylaminohydrochloride in pyridine.

Melting point: 229 to 231° C. (acetone)

$α_D$=+298° (CHCl$_3$)

$^1$H-NMR spectrum in CDCl$_3$ [δ, ppm]: 0.54 (s, 3H, H-18); 1.63 (s, 1H, OH), 4.36 (s, 1H, 17α), 4.43 (d, J=8.0 Hz, 1H, H-11α), 5.72 (d, 1H, J=6.4 Hz, olefin, proton), 5.79 (s, 1H, H-4), 5.93 (d, 1H, J=6.4 Hz, olefin, proton), 7.19 and 7.48 (2d, 4H, J=8.4 and 8.8 Hz, A,A', B,B'-system of aromatic compound protons), 7.61 (s, 1H, NOH), 8.09 (s, 1H, CH=N—).

Production of the Starting Compound 4.8 g of 3,3-dimethoxy-11β-{[4-(1,1-ethylenedioxy)methyl]phenyl}-5α-hydroxy-estr-9-en-17-one is dissolved in 180 ml of THF. At −70° C., 15 ml of a 2 M solution of lithium diisopropylamide in THF/heptane/ethylbenzene and 5.1 ml of trimethylchlorosilane are added in drops in succession under argon protection. It is allowed to come to room temperature, stirred into aqueous sodium bicarbonate solution, extracted with ethyl acetate and worked up as usual. The 4-(3,3-dimethoxy-5α-hydroxy-17-trimethylsilyloxy-estra-9,15-dien-11β-yl)benzaldehyde-ethylene acetal is isolated as a yellow foam. 6.1 g of the crude product is dissolved in 50 ml of acetonitrile, mixed with 2.47 g of palladium(II)-acetate, stirred for 4 hours at room temperature, filtered on diatomaceous earth, concentrated by evaporation, chromatographed and recrystallized from tert-butyl methyl ether.

961 mg of the 4-(3,3-dimethoxy-5α-hydroxy-17-oxoestra-9,15-dien-11β-yl)benzaldehyde-ethylene acetal that is obtained in this case is dissolved in 5 ml of methanol, cooled to −10° C., and mixed with 30 mg of sodium bicarbonate and then with 745 mg of $CeCl_3 \times 7\ H_2O$ and 348 mg of sodium borohydride in 20 ml of methanol. It is stirred into ice water after 20 minutes, the 4-(5α,17β-dihydroxy-3,3-dimethoxy-estra-9,15-dien-11β-yl)benzaldehyde-ethylene acetal is suctioned off, rewashed with water, and the substance is dissolved with acetone. After 1 ml of water and 150 mg of p-toluenesulfonic acid are added, the protective groups are cleaved off and stirred into ice water after 2 hours. The 4-(17β-hydroxy-3-oxoestra-4,9,15-trien-11β-yl)benzaldehyde is suctioned off, dried and recrystallized after chromatography from acetone.

Melting point: 180 to 183° C. (acetone)
$α_D$=+162° ($CHCl_3$)
$^1$H-NMR spectrum in $CDCl_3$ [δ, ppm]: 0.53 (s, 3H, H-18), 1.63 (s, 1H, OH), 4.37 (s, 1H, H-17α), 4.50 (d, 1H, J=7.6 Hz, H-11α), 5.72 (d, 1H, olefin, proton), 5.80 (s, 1H, H-4), 5.93 (d, 1H, J=7.67 Hz, olefin, proton), 7.36 and 7.80 (2d, 4H, J=8.0 Hz, and 8.8 Hz, A,A', B,B'-system of the aromatic compound protons), 9.96 (s, 1H, CH=O).

EXAMPLE 13

4-(17β-Acetoxy-4'-bromo-3-oxoestra-4,9-dien-11β-yl)benzaldehyde-1-(E)oxime 528 mg of 4-(4'-bromo-17β-hydroxy-3-oxoestra-4,9-dien-11β-yl)benzaldehyde is acetylated according to Example 3 and then oximized according to Example 1.

Melting point: 158-161° C. (decomposition, acetone)
$α_D$=+155° ($CHCl_3$)
$^1$H-NMR spectrum in $CDCl_3$ [δ, ppm]: 0.48 (s, 3H, H-18), 2.04 (s, 3H, $COCH_3$), 4.35 (d, J=7.6 Hz, 1H, H-11α), 4.62 (t, 1H, J=7.6 Hz, H17α), 7.16 and 7.49 (2d, 4H, J=8.0 and 8.8 Hz, A,A', B,B'-system of the aromatic compound protons), 7.92 (s, 1H, NOH), 8.10 (s, 1H, CH=N—).

EXAMPLE 14

4-(17β-Acetoxy-4'-bromo-3-oxoestra-4,9-dien-11β-yl)benzaldehyde-1-(E)-O-acetyloxime 100 mg of 4-(17β-acetoxy-4-bromo-3-oxoestra-4,9-dien-11β-yl)benzaldehyde-1[E]-oxime is acetylated according to Example 3.

Melting point: 114 to 118° C. (diethyl ether/n-hexane)
$α_D$=+147° ($CHCl_3$)
$^1$H-NMR spectrum in $CDCl_3$ [δ, ppm]: 0.45 (s, 3H, H-18), 2.03 and 2.23 (2s, 2×3H, 2×$COCH_3$), 4.37 (d, J=7.2 Hz, 1H, H-11α), 4.62 (t, 1H, J=8.4 Hz, H-17α), 7.22 and 7.65 (2d, 4H, J=8.0 Hz, A,A', B,B'-system of the aromatic compound protons), 8.32 (s, 1H, CH=N—).

EXAMPLE 15

4-(17β-Ethoxy-3-oxoestra-4,9-dien-11β-yl)benzaldehyde-1(E)-oxime

From 4-(17β-ethoxy-3-oxoestra-4,9-dien-11β-yl)benzaldehyde with hydroxylamine-hydrochloride in pyridine according to Example 1

Melting point: 100 to 103° C. (acetone) $α_D$=+256° ($CHCl_3$)
$^1$H-NMR spectrum in $CDCl_3$ [δ, ppm]: 0.44 (s, 3H, H-18), 1.71 (t, 3H, $CH_2CH_3$), 3.33 (t, 1H, J=8.0 Hz, 17α-H), 3.5 (m, 2H, $CH_2CH_3$), 4.34 (d, J=7.6 Hz, 1H, H-11α), 5.77 (s, 1H, H-4), 7.20 (d, 2H, J=8.0 Hz aromatic compound protons), 7.48 (d, 2H, J=8.4 Hz, aromatic compound protons), 7.69 (s, 1H NOH), 8.10 (s, 1H, CH=N—).

Production of the Starting Compound

Analogously to Example 5 from 4-(3,3-dimethoxy-5α,17β-dihydroxy-estr-9-en-11β-yl)-benzaldehyde-neopentylacetal and ethyl bromide and potassium-tert-butanolate in THF to form 4-(3,3-dimethoxy-17β-ethoxy-5α-hydroxy-estr-9-en-11β-yl)benzaldehyde-neopentyl acetal.

Melting point: 161 to 168° C. (methanol)
$α_D$=+15° ($CHCl_3$)
$^1$H-NMR spectrum in $CDCl_3$ [δ, ppm]: 0.36 (s, 3H, H-18), 0.86 and 1.03 (2s; 3H, 3-acetal $CH_3$ each), 1.14 (t, 3H, $CH_2CH_3$), 3.26 (t, 1H, J=8.0 Hz, 17α-H), 3.3 (2s, 6H, 2×$OCH_3$), 3.48 to 3.57 (m, 6H, 3×$CH_2$), 4.22 (d, 1H, H-11α), 4.39 [s, 1H, CH—$(OR)_2$], 5.35 (s, 1H, OH), 7.21 (d, 2H, J=8.0 Hz aromatic compound protons), 7.31 (d, 2H, J=8.4 Hz, aromatic compound protons)

Subsequent hydrolysis to form 4-(17β-ethoxy-3-oxoestra-4,9-dien-11β-yl)benzaldehyde Melting point: 149 to 152° C. (tert-butyl methyl ether)
$α_D$=+216° ($CHCl_3$);
$^1$H-NMR spectrum in $CDCl_3$ [δ, ppm]: 0.42 (s, 3H, H-18), 1.16 (t, 3H, ethyl-$CH_3$), 3.31 (t, 1H, J=8.4 Hz, 17α-H), 3.48 (q, 2H, $CH_2CH_3$), 4.40 (d, J=7.6 Hz, 1H, H-11α), 5.78 (s, 1H, H-4), 7.37 (d, 2H, J=8.0 Hz, aromatic compound protons), 7.80 (d, 2H, J=8.4 Hz, aromatic compound protons), 8.96 (s, 1H, CH=O).

EXAMPLE 16

4-(17β-Benzoyloxy-3-oxoestra-4,9-dien-1β-yl)benzaldehyde-1(E)-oxime

Analogously to Example 3 from 4-(17β-hydroxy-3-oxoestra-4,9-dien-11β-yl)benzaldehyde and benzoyl chloride in pyridine and subsequent oximization with hydroxylamino-hydrochloride in pyridine according to Example 1.

Melting point: 132 to 133° C. (acetone)
$α_D$=+219° ($CHCl_3$);
$^1$H-NMR spectrum in $CDCl_3$ [δ, ppm]: 0.61 (s, 3H, H-18), 4.38 (d, J=7.6 Hz, 1H, H-11α), 4.89 (t, 1H, 17α-H), 5.79 (s, 1H, H-4), 7.19 (d, 2H, J=8.4 Hz, aromatic compound protons), 7.40-7.55 (m, 5H, aromatic compound), 7.99 (d, 2H, J=8.0 Hz, aromatic compound protons), 8.09 (s, 1H, CH=N—).

EXAMPLE 17

4-(17β-Benzyloxy-3-oxoestra-4,9-dien-11β-yl)benzaldehyde-1(E)-oxime

Analogously to Example 1 from 4-(17β-benzyloxy-3-oxoestra-4,9-dien-11β-yl)benzaldehyde and hydroxylaminohydrochloride in pyridine.

Melting point: 103 to 109° C. (acetone)

$^1$H-NMR spectrum in CDCl$_3$ [δ, ppm]: 0.51 (s, 3H, H-18), 3.42 (t, J=8.0 Hz, H-17α), 4.33 (d, J=7.6 Hz, 1H, H-11α), 4.49 (q, 2H, PhCH$_2$), 5.76 (s, 1H, H-4), 7.19 (d, 2H, J=8.0 Hz, aromatic compound protons), 7.25-7.34 (m, 5H, aromatic compound), 7.48 (d, 2H, J=8.4 Hz, aromatic compound protons), 8.09 (s, 1H, CH=N—).

Production of the Starting Material 790 mg of [4-(3,3-dimethoxy-5α,17β-dihydroxy-estr-9-en-11β-yl)benzaldehyde-neopentylketal] is reacted in 15 ml of toluene with 1 ml of benzyl bromide in the presence of 675 mg of potassium tert-butanolate according to Example 5. The crude product is hydrolyzed in 8 ml of acetone with 100 mg of p-toluenesulfonic acid within 3 hours to 4-(17β-benzyloxy-3-oxoestra-4,9-dien-11β-yl)benzaldehyde.

Melting point: 83 to 87° C. (acetone)

$^1$H-NMR spectrum in CDCl$_3$ [δ, ppm]: 0.48 (s, 3H, H-18), 3.42 (t, 1H, H-17α), 4.39 (d, J=7.6 Hz, 1H, H-11α), 4.52 (q, 2H, J=12.0 Hz, J=35.6 Hz, CH$_2$Ph), 5.77 (s, 1H, H-4), 7.29-7.35 (m, 5H, aromatic compound), 7.36 (d, 2H, J=8.4 Hz, aromatic compound protons), 7.80 (d, 2H, J=8.0 Hz, aromatic compound protons), 9.96 (s, 1H, CH=O).

EXAMPLE 18

4-(17β-Methoxy-3-oxoestra-4,9-dien-11β-yl)benzaldehyde-1(E)-[(N-ethyl)-carbonyl]oxime Analogously to Example 1 from 4-(17β-methoxy-3-oxoestra-4,9-dien-11β-yl]benzaldehyde-1-(E)-oxime with ethyl isocyanate in toluene.

Melting point: 175 to 176° C.

α$_D$=+291° (CHCl$_3$)

$^1$H-NMR spectrum in CDCl$_3$ [δ, ppm]: 0.42 (s, 3H, H-18), 1.23 (t, 3H, ethyl), 3.25 (t, 1H, H-17α), 3.34 (s, 3H, OCH$_3$), 3.37 (q, 2H, CH$_2$CH$_3$), 4.38 (d, J=7.6 Hz, 1H, H-11α), 5.78 (s, 1H, H-4), 6.21 (t, 1H, NH), 7.26 (d, 2H, J=8.4 Hz, aromatic compound protons), 7.58 (s, 2H, J=8.0 Hz, aromatic compound protons), 8.28 (s, 1H, CH=N—).

EXAMPLE 19

4-(4'-Bromo-17β-hydroxy-3-oxoestra-4,9-dien-11β-yl)benzaldehyde-1(E)-oxime

Analogously to Example 1 from 4-(4'-bromo-17β-hydroxy-3-oxoestra-4,9-dien-11β-yl)benzaldehyde and hydroxylaminohydrochloride in pyridine.

Melting point: Starting from 273° C. (decomposition, ether)

α$_D$=+209° (CHCl$_3$)

$^1$H-NMR spectrum in CDCl$_3$ [δ, ppm] 0.44 (s, 3H, H-18), 3.68 (t, 1H, H-17α), 4.36 (d, J=6.8 Hz, 1H, H-11α), 7.17 and 7.47 (2d, 4H, J=8.0 Hz, A,A', B,B'-system of the aromatic compound protons), 8.09 (s, 1H, CH=N—), 8.35 (s, 1H, NOH).

Production of the Starting Compound 4-(17β-Hydroxy-3-oxoestra-4,9-dien-11β-yl)benzaldehyde is reacted according to Example 5 in THF with NBS to form 4-(4'-bromo-17β-hydroxy-3-oxoestra-4,9-dien-11β-yl)benzaldehyde and purified by chromatography. The purified product is incorporated directly into the oximization.

$^1$H-NMR spectrum in CDCl$_3$ [δ, ppm]: 0.52 (s, 3H, H-18), 1.27 (s, 3H, 17α-CH$_3$), 3.21 (2t, 1H, OH), 4.41 (d, J=7.2 Hz, 1H, H-11α), 7.34 and 7.79 (2d, 4 H, J=8.0 Hz, A,A', B,B'-system of the aromatic compound protons), 9.96 (s, 1H, CH=O).

EXAMPLE 20

4-[17β-Hydroxy-17α-hydroxymethyl-3-oxoestra-4,9-dien-11β-yl]benzaldehyde-1-(E)-[O-(ethylamino)-carbonyl]oxime 1.5 g of 4-[17β-hydroxy-17α-(tetrahydrohydropyranoyloxy)methyl-3-oxoestra-4,9-dien-11β-yl]benzaldehyde-1-(E)-[O-(ethylamino)-carbonyl]oxime is dissolved in 30 ml of glacial acetic acid and stirred for 24 hours at 50° C. Then, it is added in drops in aqueous NaHCO$_3$ solution, extracted with ethyl acetate, the organic phase is washed with water and dried on Na$_2$SO$_4$. The solvent is vacuum-evaporated, and the crystalline residue (1.33 g) is purified by flash chromatography on silica gel with a toluene/acetone mixture.

Melting point: 164 to 166° C. (acetone)

α$_D$=+258° (CHCl$_3$)

$^1$H-NMR spectrum in CDCl$_3$+D$_2$O [δ, ppm]: 0.55 (s, 3H, H-18), 1.23 (t, 3H, CH$_2$CH$_3$), 1.62 (s, 3H, CH$_3$), 3.37 (m, 2H, CH$_2$), 3.35 and 3.79 (2d, 2H, J=10.8 Hz, CH$_2$OH), 4.42 (d, J=7.2 Hz, 1H, H-11α), 5.78 (s, 1H, H-4), 7.26 (d, 2H, J=8.0 Hz, aromatic compound protons), 7.58 (d, 2H, J=8.0 Hz, aromatic compound protons), 8.28 (s, 1H, CH=NOR).

Production of the Starting Compound

Step 1

Analogously to Example 9,4-(3,3-dimethoxy-5α-hydroxy-17-oxoestr-9-en-11β-yl)benzaldehyde-ethylene acetal is converted into 4-(3,3-dimethoxy-5α-hydroxy-17-(S)-spiroepoxy-estr-9-en-11β-yl)benzaldehyde-ethylene acetal.

19.4 g of 4-(3,3-dimethoxy-5α-hydroxy-17-(S)-spiroepoxy-estr-9-en-11β-yl)-benzaldehyde-ethylene acetal is dissolved in 250 ml of N-methyl-2-pyrrolidone. 145 ml of 2 N aqueous NaOH is added, it is heated for 2 hours to 100° C., cooled, and added in drops in 250 ml of aqueous 10% NH$_4$Cl solution. After extraction with ethyl acetate, the organic phase is washed neutral, dried and vacuum-evaporated.

19.5 g (yield 65%) of 4-(3,3-dimethoxy-5α,17β-dihydroxy-17α-hydroxymethyl-estr-9-en-11β-yl)benzaldehyde-ethylene acetal is obtained as a crude product.

$^1$H-NMR spectrum in CDCl$_3$+D$_2$O [δ, ppm]: 0.47 (s, 3H, H-18), 3.21 and 3.22 (2s; 3H, and OCH$_3$ each), 3.40 and 3.74 (2d, 2H, J=10.8 Hz, CH$_2$OH), 4.07 (m, 4H, ethylene acetal), 4.42 (d, J=7.2 Hz, 1H, H-11α), 5.76 (s, 1H, benzaldehyde acetal), 7.23 (d, 2H, J=8.0 Hz, aromatic compound protons), 7.37 (d, 2H, J=8.0 Hz, aromatic compound protons).

This product is dissolved in 120 ml of tetrahydrofuran, mixed with 12 ml of water and 5.3 g of p-toluenesulfonic acid, and stirred for 4 hours at room temperature. Then, the solution is neutralized with aqueous NaHCO$_3$ solution, and 8.5 g of 4-[17β-hydroxy-17α-(hydroxymethyl)-3-oxoestra-4,9-dien-11β-yl]benzaldehyde is isolated as a light yellow foam, which is purified by flash chromatography, with ethyl acetate according to the commonly used working-up process (yield 65%).

Melting point: 116 to 123° C. (acetone)

$\alpha_D$=+185° (CHCl$_3$)

$^1$H-NMR spectrum in CDCl$_3$ [δ, ppm]: 0.60 (s, 3H, H-18), 3.43 and 3.79 (2d, 2H, J=10.8 Hz, CH$_2$OH), 4.32 (d, J=7.4 Hz, 1H, H-11α), 5.74 (s, 1H, H-4), 6.67 (d, 2H, J=8.0 Hz, aromatic compound protons), 7.00 (d, 2H, J=8.0 Hz, aromatic compound protons), 9.98 (CHO).

Step 2

5.4 g of 4-[17β-hydroxy-17α-(hydroxymethyl)-3-oxoestra-4,9-dien-11β-yl]benzaldehyde is reacted in 50 ml of methylene chloride with 16.9 ml of 3,4-dihydro-2H-pyran and 335 mg of pyridinium-4-toluenesulfonate within 1 hour at room temperature. Then, the solution is stirred in 100 ml of saturated aqueous NaHCO$_3$ solution, extracted with methylene chloride, the organic solution is washed neutral, dried on Na$_2$SO$_4$, filtered off, and the solvent is concentrated by evaporation under vacuum. 7.3 g of a mixture that consists of 4-[17β-hydroxy-17α-(tetrahydroxypyranyloxy)methyl-3-oxoestra-4,9-dien-11β-yl]benzaldehyde and 4-[17β-tetrahydropyranyloxy,17α-(tetrahydroxypyranyloxy)methyl-3-oxoestra-4,9-dien-11β-yl]benzaldehyde is obtained. After flash chromatography on silica gel with a toluene/acetone gradient, 4.7 g of 4-[17β-hydroxy-17α-(tetrahydroxypyranyloxy)methyl-3-oxoestra-4,9-dien-11β-yl]benzaldehyde is isolated.

LC/MS purity: 491 (M$^+$+1) 99% surface area (isomer mixture, THP-monoether 87% and 12%)

$^1$H-NMR spectrum in CDCl$_3$ [δ, ppm]: 0.53 (s, 3H, H-18), 4.44 (d, J=6.4 Hz, 1H, H-11α), 4.56 and 4.60 (2t, 2H, CH$_2$OH), 5.79 (s, 1H, H-4), 7.36 (d, 2H, J=8.0 Hz, aromatic compound protons), 7.79 (d, 2H, J=8.0 Hz, aromatic compound protons), 9.95 (CHO).

Step 3

Analogously to Example 1, 4.8 g of 4-[17β-hydroxy-17α-(tetrahydroxypyranyloxy)methyl-3-oxoestra-4,9-dien-11β-yl]benzaldehydoxime is obtained from 4.75 g of 4-[17β-hydroxy-17α-(tetrahydroxypyranyloxy)-methyl-3-oxoestra-4,9-dien-11β-yl]benzaldehyde and 603 mg of hydroxylaminohydrochloride in 45 ml of pyridine, which are purified by flash chromatography on silica gel with a toluene/acetone gradient.

LC/MS purity: 491 (M$^+$+1) 99% surface area (isomer mixture, THP-monoether −93% and 6%)

$^1$H-NMR spectrum in CDCl$_3$ [δ, ppm]: 0.88 (s, 3H, H-18), 4.44 (d, J=6.4 Hz, 1H, H-11α), 4.55 and 4.60 (2t, 2H, CH$_2$OH), 5.77 (s, 1H, H-4), 7.19 (d, 2H, J=8.4 Hz, aromatic compound protons), 7.46 (d, 2H, J=8.4 Hz, aromatic compound protons), 8.09 (CH=NOH).

Step 4

Analogously to Example 4, 1.54 g of 4-[17β-hydroxy-17α-(tetrahydrohydropyranoyloxy)methyl-3-oxoestra-4,9-dien-11β-yl]benzaldehyde-1-(E)-[O-(ethylamino)-carbonyl] oxime is obtained from 1.32 g of 4-[17β-hydroxy-17α-(tetrahydroxypyranyloxy)methyl-3-oxoestra-4,9-dien-11β-yl]benzaldehydoxime with ethyl isocyanate in toluene as a crude product, which is used without further purification in the final step.

$^1$H-NMR spectrum in CDCl$_3$ [δ, ppm]: 0.55 (s, 3H, H-18), 1.23 (t. 3H. CH$_2$CH$_3$), 3.4 (m, 2 H, CH$_2$CH$_3$), 4.44 (m, 1H, H-11α), 4.6 and 4.90 (2m, 2H, CH$_2$OR), 5.77 (s, 1H, H-4), 6.22 (s, 1H, NH), 7.26 (d, 2H, J=8.4 Hz, aromatic compound protons), 7.57 (d, 2H, J=8.4 Hz, aromatic compound protons), 8.29 (CH=NOR).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius, and all parts and percentages are by weight, unless otherwise indicated.

The entire disclosure of all applications, patents and publications, cited herein and of corresponding U.S. Provisional Application Ser. No. 60/400,065, filed Aug. 2, 2002, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The invention claimed is:

1. A compound of formula I

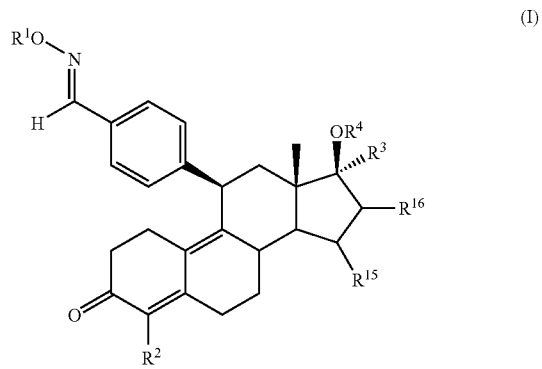

wherein R$^1$, R$^2$, R$^3$, R$^4$ and R$^5$ as well as R$^{15}$ and R$^{16}$ have the following meaning:

R$^1$ is a hydrogen atom, an alkanoyl radical with 1 to 10 carbon atoms or an optionally substituted benzoyl radical with 6-10 carbon atoms or a radical CONHR$^5$, wherein R$^5$ is a hydrogen atom, an alkyl or acyl radical which comprises 1-10 carbon atoms in each case or an alkylaryl or aralkyl radical which comprises 6-10 carbon atoms in each case, R$^2$ is a halogen atom or a CF$_3$ group, R$^3$ is a hydrogen atom or a group CH$_2$X, wherein X is a hydrogen atom, a hydroxy group, a halogen atom, an alkyl radical with 1 or 2 carbon atoms, or X is a radical (CH$_2$)$_n$CH$_2$Y wherein n=0 or 1, and Y is a halogen atom, wherein if R$^2$ is a halogen atom, R$^3$ optionally is additionally a group C$_n$F$_m$H$_o$, wherein n=1, 2, 3, 4 or 5, m>1 and m+o=2n+1, R$^4$ is a hydrogen atom, an alkyl or alkanoyl radical that consists of 1-10 carbon atoms in each case or a benzoyl radical which comprises 6-10 carbon atoms or a radical —CONHR⁵, wherein R⁵ has the above-indicated meaning, and R¹⁵ and R¹⁶ are each, independently of one another, hydrogen or together a double bond.

2. A compound of formula 1 according to claim 1, wherein R² is a chlorine or bromine atom.

3. A compound of formula I according to claim 1, wherein R³ is a hydrogen atom or a group CH₂X, in which X is a hydrogen atom, a hydroxy group, a halogen atom, or a straight-chain or branched or unsaturated alkyl radical with 1-2 carbon atoms, a radical (CH₂)ₙCH₂Y wherein n=0 or 1, and Y is a halogen atom.

4. A compound of formula I, according to claim 1, wherein R⁴ is a hydrogen atom or an alkyl radical with 1 to 4 carbon atoms.

5. A compound of formula I according to claim 1, in which R¹ is a hydrogen atom, R² is a chlorine atom or a bromine atom, and R³ is a hydrogen atom, a methyl group, or a CH₂-X group, wherein X is a fluorine, chlorine or bromine atom or a hydroxy group.

6. A compound of formula I, according to claim 1, which is:

4-[4'-Bromo-17β-hydroxy-3-oxoestra-4,9-dien-11β-yl]benzaldehyde-1-(E)-oxime,

4-[4'-Bromo-17β-hydroxy-17α-methyl-3-oxoestra-4,9-dien-11β-yl]benzaldehyde-1-(E)-oxime, 4-[4'-Bromo-17β-hydroxy-17α-trifluoromethyl-3-oxoestra-4,9-dien-11β-yl]benzaldehyde-1-(E)-oxime, 4-[17β-Acetoxy-4'-bromo-3-oxoestra-4,9-dien-11β-yl]benzaldehyde-1-(E)-oxime, 4-[17β-Acetoxy-4'-bromo-3-oxoestra-4,9-dien-11β-yl]benzaldehyde-1-(E)-O-acetyloxime, 4-[4'-Chloro-17β-hydroxy-17α-trifluoromethyl-3-oxoestra-4,9-dien-11β-yl]benzaldehyde-1-(E)-oxime, 4-[4'-Chloro-17β-hydroxy-3-oxoestra-4,9-dien-11β-yl]benzaldehyde-1-(E)-oxime, 4-[4'-Bromo-17α-fluoromethyl-17β-hydroxy-3-oxoestra-4,9-dien-11β-yl]benzaldehyde-1-(E)-oxime, 4-[4'-Bromo-17α-chloromethyl-17β-hydroxy-3-oxoestra-4,9-dien-11β-yl]benzaldehyde-1-(E)-oxime, 4-[4'-Bromo-17α-bromomethyl-17β-hydroxy-3-oxoestra-4,9-dien-11β-yl]benzaldehyde-1-(E)-oxime, 4-[4'-Chloro-17β-methoxy-3-oxoestra-4,9-dien-11β-yl]benzaldehyde-1-(E)-oxime, 4-[4'-Chloro-17α-chloromethyl-17β-hydroxy-3-oxoestra-4,9-dien-11β-yl]benzaldehyde-1-(E)-oxime, 4-[17β-Methoxy-4'-trifluoromethyl-3-oxoestra-4,9-dien-11β-yl]benzaldehyde-1-(E)-oxime, or 4-[4'-Chloro-17β-hydroxy-17α-methyl-3-oxoestra-4,9-dien-11β-yl]benzaldehyde-1(E)-oxime.

7. A pharmaceutical composition comprising at least one compound of formula I according to claim 1 and a pharmaceutically compatible vehicle.

8. A method for female birth control, for treating dysfunctional bleeding, for treating dysmenorrhea, for inducing an amenorrhea, or for treating hormonal disorders in postmenopausal women, comprising administering to a female

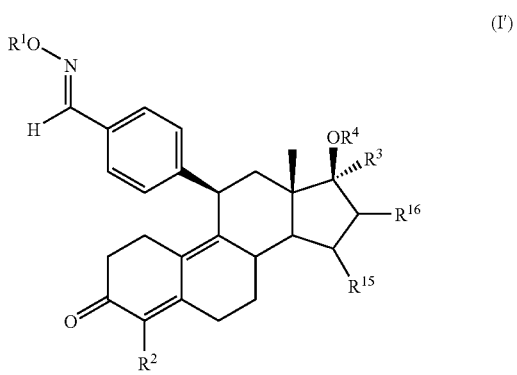

a compound of formula I' wherein R¹, R², R³, R⁴ and R⁵ as well as R¹⁵ and R¹⁶ have the following meaning:

R¹ is a hydrogen atom, an alkanoyl radical with 1 to 10 carbon atoms or an optionally substituted benzoyl radical with 6-10 carbon atoms or a radical CONHR⁵, wherein R⁵ is a hydrogen atom, an alkyl or acyl radical which comprises 1-10 carbon atoms in each case or an alkylaryl or aralkyl radical which comprises 6-10 carbon atoms in each case, R² is a halogen atom or a CF₃ group, R³ is a hydrogen atom or a group CH₂X, wherein X is a hydrogen atom, a hydroxy group, a halogen atom, an alkyl radical with 1 or 2 carbon atoms, or X is a radical (CH₂)ₙCH₂Y wherein n=0 or 1, and Y is a halogen atom, wherein if R² is a halogen atom, R³ optionally is additionally a group CₙFₘHₒ, wherein n=1, 2, 3, 4 or 5, m>1 and m+o=2n+1, R⁴ is a hydrogen atom, an alkyl or alkanoyl radical that consists of 1-10 carbon atoms in each case or a benzoyl radical which comprises 6-10 carbon atoms or a radical —CONHR⁵, wherein R⁵ has the above-indicated meaning, and R¹⁵ and R¹⁶ are each, independently of one another, hydrogen or together a double bond.

9. A method for treating dysfunctional bleeding according to claim 8, comprising administering to a host in need thereof a compound of formula I'.

10. A method for treating dysmenorrhea according to claim 8, comprising administering to a host in need thereof a compound of formula I'.

11. A method for inducing an amenorrhea according to claim 8, comprising administering to a host in need thereof a compound of formula I'.

12. A method for treating hormonal disorders in postmenopausal women according to claim 8, comprising administering to a host in need thereof a compound of formula I'.

13. A process for treating endometriosis or uterus myomatoses, comprising administering to a host in need thereof a compound of claim 1.

14. A method according to claim 8, wherein the compound is administered in combination with at least one low-dose natural or synthetic estrogen.

15. A method according to claim 14, comprising using an estrogen as its 3-sulfamate.

16. A method according to claim 15, wherein the estrogen-3-sulfamate is 17β-hydroxy-estra-1,3,5(10)-trien-3yl-sulfamate.

17. A method for the production of a pharmacological agent, comprising bringing together a compound of claim 1 and a pharmacologically acceptable carrier.

18. A method for female birth control, comprising administering to a female a compound according to claim 1.

19. A method according to claim 18, wherein the compound is administered in combination with at least one low-dose natural or synthetic estrogen.

20. A method according to claim 19, comprising using an estrogen as its 3-sulfamate.

21. A method according to claim 13, wherein the compound is administered in combination with at least one low-dose natural or synthetic estrogen.

22. A method according to claim 21, comprising using an estrogen as its 3-sulfamate.

23. A compound of formula I

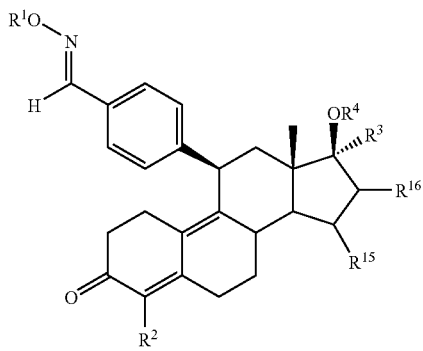

(I)

wherein $R^1$, $R^2$, $R^3$, $R^4$ and $R^5$ as well as $R^{15}$ and $R^{16}$ have the following meaning:

$R^1$ is a hydrogen atom, an alkanoyl radical with 1 to 10 carbon atoms or an optionally substituted benzoyl radical with 6-10 carbon atoms or a radical $CONHR^5$, wherein $R^5$ is a hydrogen atom, an alkyl or acyl radical which comprises 1-10 carbon atoms in each case, or an alkylaryl or aralkyl radical which comprises 6-10 carbon atoms in each case, $R^3$ is a halogen atom or a $CF_3$ group, $R^3$ is a hydrogen atom or a group $CH_2X$, wherein X is a hydrogen atom, a hydroxy group, a halogen atom, an alkyl radical with 1 or 2 carbon atoms, or X is a radical $(CH_2)_nCH_2Y$ wherein n=0 or 1, and Y is a halogen atom, wherein if $R^2$ is a halogen atom, $R^3$ optionally is additionally a group $C_nF_mH_o$, wherein n=1, 2, 3, 4 or 5, m>1 and m+o=2n+1, $R^4$ is a hydrogen atom, an alkyl or alkanoyl radical that consists of 1-10 carbon atoms in each case or a benzoyl radical which comprises 6-10 carbon atoms or a radical $CONHR^5$, wherein $R^5$ has the above-indicated meaning, and $R^{15}$ and $R^{16}$ are each, independently of one another, hydrogen or together a double bond, or a pharmaceutically acceptable salt thereof.

24. A method for female birth control, for treating dysfunctional bleeding, for treating dysmenorrhea, for inducing an amenorrhea, or for treating hormonal disorders in postmenopausal women, comprising administering to a female a compound according to claim 23.

* * * * *